US 9,646,375 B2

(12) United States Patent
Satish et al.

(10) Patent No.: US 9,646,375 B2
(45) Date of Patent: May 9, 2017

(54) METHOD FOR SETTING A BLOOD TRANSFUSION PARAMETER

(71) Applicant: Gauss Surgical, Inc., Los Altos, CA (US)

(72) Inventors: Siddarth Satish, Cupertino, CA (US); Kevin Miller, Mountain View, CA (US); Ali Zandifar, San Francisco, CA (US)

(73) Assignee: Gauss Surgical, Inc., Los Altos, CA (US)

( * ) Notice: Subject to any disclaimer, the term of this patent is extended or adjusted under 35 U.S.C. 154(b) by 0 days.

(21) Appl. No.: 14/072,632

(22) Filed: Nov. 5, 2013

(65) Prior Publication Data
US 2014/0128838 A1    May 8, 2014

Related U.S. Application Data

(60) Provisional application No. 61/722,780, filed on Nov. 5, 2012.

(51) Int. Cl.
*G06K 9/00* (2006.01)
*G06T 7/00* (2017.01)
*A61M 1/02* (2006.01)
*A61M 1/00* (2006.01)

(52) U.S. Cl.
CPC ......... *G06T 7/0012* (2013.01); *A61M 1/0001* (2013.01); *A61M 1/024* (2013.01); *A61M 2202/0429* (2013.01); *A61M 2205/3306* (2013.01); *A61M 2205/3379* (2013.01); *G06T 2207/10024* (2013.01); *G06T 2207/30024* (2013.01)

(58) Field of Classification Search
None
See application file for complete search history.

(56) References Cited

U.S. PATENT DOCUMENTS

| 2,707,955 A | 5/1955 | Borden |
| 3,182,252 A | 5/1965 | Den Berg |
| 3,199,507 A | 8/1965 | Kamm |

(Continued)

FOREIGN PATENT DOCUMENTS

| CA | 2870635 A1 | 10/2013 |
| CN | 101505813 | 8/2009 |

(Continued)

OTHER PUBLICATIONS

Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>.

(Continued)

*Primary Examiner* — Weiwen Yang

(57) ABSTRACT

One variation of a method for setting a blood transfusion parameter for a patient includes identifying a blood transfusion bag in a photographic image; extracting a color feature from a region of the photographic image corresponding to the blood transfusion bag; estimating a blood component content within the blood transfusion bag based on the color feature; and triggering transfusion from the blood transfusion bag based on the blood component content within the blood transfusion bag and an estimated volemic status of the patient.

28 Claims, 11 Drawing Sheets

(56) References Cited

U.S. PATENT DOCUMENTS

| | | | |
|---|---|---|---|
| 3,367,431 | A | 2/1968 | Prindle Baker |
| 3,646,938 | A | 3/1972 | Haswell |
| 3,832,135 | A * | 8/1974 | Chlupsa et al. ............... 436/47 |
| 3,864,571 | A | 2/1975 | Stillman et al. |
| 3,948,390 | A | 4/1976 | Ferreri |
| 4,105,019 | A | 8/1978 | Haswell |
| 4,149,537 | A | 4/1979 | Haswell |
| 4,244,369 | A | 1/1981 | McAvinn et al. |
| 4,402,373 | A | 9/1983 | Comeau |
| 4,422,548 | A | 12/1983 | Cheesman et al. |
| 4,429,789 | A | 2/1984 | Puckett |
| 4,562,842 | A | 1/1986 | Morfeld et al. |
| 4,583,546 | A | 4/1986 | Garde |
| 4,773,423 | A | 9/1988 | Hakky |
| 4,784,267 | A | 11/1988 | Gessler et al. |
| 4,832,198 | A | 5/1989 | Alikhan |
| 4,917,694 | A | 4/1990 | Jessup |
| 4,922,922 | A | 5/1990 | Pollock et al. |
| 5,029,584 | A | 7/1991 | Smith |
| 5,031,642 | A | 7/1991 | Nosek |
| 5,048,683 | A | 9/1991 | Westlake |
| 5,119,814 | A | 6/1992 | Minnich |
| 5,132,087 | A | 7/1992 | Manion et al. |
| 5,190,059 | A | 3/1993 | Fabian et al. |
| 5,231,032 | A | 7/1993 | Ludvigsen |
| 5,236,664 | A | 8/1993 | Ludvigsen |
| 5,285,682 | A | 2/1994 | Micklish |
| 5,492,537 | A | 2/1996 | Vancaillie |
| 5,522,805 | A | 6/1996 | Vancaillie et al. |
| 5,629,498 | A | 5/1997 | Pollock et al. |
| 5,633,166 | A | 5/1997 | Westgard et al. |
| 5,650,596 | A | 7/1997 | Morris et al. |
| 5,709,670 | A | 1/1998 | Vancaillie et al. |
| 5,807,358 | A | 9/1998 | Herweck et al. |
| 5,851,835 | A | 12/1998 | Groner |
| 5,923,001 | A | 7/1999 | Morris et al. |
| 5,931,824 | A | 8/1999 | Stewart et al. |
| 5,944,668 | A | 8/1999 | Vancaillie et al. |
| 5,956,130 | A | 9/1999 | Vancaillie et al. |
| 5,984,893 | A | 11/1999 | Ward |
| 6,006,119 | A | 12/1999 | Soller et al. |
| 6,061,583 | A | 5/2000 | Ishihara et al. |
| 6,359,683 | B1 | 3/2002 | Berndt |
| 6,510,330 | B1 | 1/2003 | Enejder |
| 6,728,561 | B2 | 4/2004 | Smith et al. |
| 6,730,054 | B2 | 5/2004 | Pierce et al. |
| 6,777,623 | B2 | 8/2004 | Ballard |
| 7,001,366 | B2 | 2/2006 | Ballard |
| 7,112,273 | B2 | 9/2006 | Weigel et al. |
| 7,147,626 | B2 | 12/2006 | Goodman et al. |
| 7,274,947 | B2 | 9/2007 | Koo et al. |
| 7,364,545 | B2 | 4/2008 | Klein |
| 7,384,399 | B2 | 6/2008 | Ghajar |
| 7,430,047 | B2 | 9/2008 | Budd et al. |
| 7,430,478 | B2 | 9/2008 | Fletcher-Haynes et al. |
| 7,469,727 | B2 | 12/2008 | Marshall |
| 7,499,581 | B2 | 3/2009 | Tribble et al. |
| 7,641,612 | B1 | 1/2010 | Mccall |
| D611,731 | S | 3/2010 | Levine |
| 7,670,289 | B1 | 3/2010 | Mccall |
| 7,703,674 | B2 | 4/2010 | Stewart et al. |
| 7,708,700 | B2 | 5/2010 | Ghajar |
| 7,711,403 | B2 | 5/2010 | Jay et al. |
| 7,749,217 | B2 | 7/2010 | Podhajsky |
| 7,795,491 | B2 | 9/2010 | Stewart et al. |
| 7,819,818 | B2 | 10/2010 | Ghajar |
| 7,909,806 | B2 | 3/2011 | Goodman et al. |
| 7,966,269 | B2 | 6/2011 | Bauer et al. |
| 7,995,816 | B2 | 8/2011 | Roger et al. |
| 8,025,173 | B2 | 9/2011 | Michaels |
| 8,181,860 | B2 | 5/2012 | Fleck et al. |
| 8,194,235 | B2 | 6/2012 | Kosaka et al. |
| 8,398,546 | B2 | 3/2013 | Pacione et al. |
| 8,472,693 | B2 | 6/2013 | Davis et al. |
| 8,576,076 | B2 | 11/2013 | Morris et al. |
| 8,626,268 | B2 | 1/2014 | Adler et al. |
| 8,693,753 | B2 | 4/2014 | Nakamura |
| 8,792,693 | B2 | 7/2014 | Satish et al. |
| 8,897,523 | B2 | 11/2014 | Satish et al. |
| 8,983,167 | B2 | 3/2015 | Satish et al. |
| 9,047,663 | B2 | 6/2015 | Satish et al. |
| 9,171,368 | B2 | 10/2015 | Satish et al. |
| 9,595,104 | B2 | 3/2017 | Satish et al. |
| 2003/0095197 | A1 | 5/2003 | Wheeler et al. |
| 2003/0130596 | A1 | 7/2003 | Goltz |
| 2004/0031626 | A1 | 2/2004 | Morris et al. |
| 2004/0129678 | A1 | 7/2004 | Crowley et al. |
| 2005/0051466 | A1 * | 3/2005 | Carter et al. ............... 210/94 |
| 2005/0163354 | A1 | 7/2005 | Ziegler |
| 2006/0058593 | A1 | 3/2006 | Drinan et al. |
| 2006/0178578 | A1 | 8/2006 | Tribble et al. |
| 2006/0224086 | A1 | 10/2006 | Harty |
| 2007/0004959 | A1 | 1/2007 | Carrier et al. |
| 2007/0287182 | A1 * | 12/2007 | Morris et al. ............... 436/2 |
| 2008/0029416 | A1 | 2/2008 | Paxton |
| 2008/0030303 | A1 | 2/2008 | Kobren et al. |
| 2008/0045845 | A1 | 2/2008 | Pfeiffer et al. |
| 2008/0194906 | A1 | 8/2008 | Mahony et al. |
| 2009/0076470 | A1 | 3/2009 | Ryan |
| 2009/0310123 | A1 | 12/2009 | Thomson |
| 2009/0317002 | A1 | 12/2009 | Dein |
| 2010/0003714 | A1 | 1/2010 | Bachur, Jr. et al. |
| 2010/0007727 | A1 | 1/2010 | Torre-Bueno |
| 2010/0025336 | A1 | 2/2010 | Carter et al. |
| 2010/0027868 | A1 | 2/2010 | Kosaka et al. |
| 2010/0066996 | A1 | 3/2010 | Kosaka et al. |
| 2010/0087770 | A1 | 4/2010 | Bock et al. |
| 2010/0152563 | A1 | 6/2010 | Turner et al. |
| 2010/0280117 | A1 | 11/2010 | Patrick et al. |
| 2011/0192745 | A1 * | 8/2011 | Min ............... A61M 1/0209 206/370 |
| 2011/0196321 | A1 | 8/2011 | Wudyka |
| 2011/0200239 | A1 | 8/2011 | Levine et al. |
| 2011/0275957 | A1 | 11/2011 | Bhandari |
| 2011/0305376 | A1 * | 12/2011 | Neff ............... 382/128 |
| 2011/0316973 | A1 | 12/2011 | Miller et al. |
| 2012/0000297 | A1 | 1/2012 | Hashizume et al. |
| 2012/0065482 | A1 | 3/2012 | Robinson et al. |
| 2012/0210778 | A1 * | 8/2012 | Palmer ............... B01L 3/5453 73/149 |
| 2012/0257188 | A1 | 10/2012 | Yan et al. |
| 2012/0262704 | A1 | 10/2012 | Zahniser et al. |
| 2012/0309636 | A1 | 12/2012 | Gibbons et al. |
| 2012/0330117 | A1 | 12/2012 | Grudic et al. |
| 2013/0010094 | A1 | 1/2013 | Satish et al. |
| 2013/0011042 | A1 | 1/2013 | Satish et al. |
| 2013/0170729 | A1 | 7/2013 | Wardlaw et al. |
| 2013/0301901 | A1 | 11/2013 | Satish et al. |
| 2013/0303870 | A1 | 11/2013 | Satish et al. |
| 2013/0308852 | A1 | 11/2013 | Hamsici et al. |
| 2014/0079297 | A1 | 3/2014 | Tadayon et al. |
| 2014/0207091 | A1 | 7/2014 | Heagle et al. |
| 2014/0330094 | A1 | 11/2014 | Pacione et al. |
| 2015/0046124 | A1 | 2/2015 | Bhavaraju et al. |
| 2015/0294460 | A1 | 10/2015 | Satish et al. |
| 2016/0027173 | A1 | 1/2016 | Satish et al. |

FOREIGN PATENT DOCUMENTS

| | | |
|---|---|---|
| JP | S-59-161801 U | 10/1984 |
| JP | S-62-144652 A | 6/1987 |
| JP | H06510210 A | 11/1994 |
| JP | H-11-37845 A | 2/1999 |
| JP | 2002-331031 A | 11/2002 |
| JP | 2003-075436 A | 3/2003 |
| JP | 2005-052288 A | 3/2005 |
| JP | 3701031 B2 | 9/2005 |
| JP | 2006-280445 A | 10/2006 |
| JP | 2008-055142 A | 3/2008 |
| JP | 2011-515681 A | 5/2011 |
| WO | 9217787 A1 | 10/1992 |
| WO | 9639927 A1 | 12/1996 |
| WO | WO-2009/117652 A1 | 9/2009 |
| WO | 2011019576 A1 | 2/2011 |

(56) References Cited

FOREIGN PATENT DOCUMENTS

| WO | 2013009709 A | 1/2013 |
|---|---|---|
| WO | 2013172874 A | 11/2013 |
| WO | 2013173356 A | 11/2013 |
| WO | WO-2014/071399 A1 | 5/2014 |

OTHER PUBLICATIONS

Kamiyoshihara, M. et al. The Utility of an Autologous Blood Salvage System in Emergency Thoracotomy for a emothorax After Chest Trauma. Gen. Thorac. Cargiovasc. Surg. (2008); vol. 56, p. 222.

Pogorelc, D. iPads in the OR: New Mobile Platform to Monitor Blood Loss During Surgery. Jun. 6, 2012. <http://medcitynews.com/2012/06/ipads-in-the-or-new-mobile-platform-to-monitor-blood-loss-during-surgery/>.

Sant, et al. "Exsanguinated Blood Volume Estimation Using Fractal Analysis of Digital Images." Journal of Forensic Sciences 57.3 (2012): 610-17. Print.

Bellad, M.B. et al. (2009). "Standardized Visual Estimation of Blood Loss during Vaginal Delivery with Its Correlation Hematocrit Changes—A Descriptive Study." South Asian Federation of Obstetrics and Gynecology 1:29-34.

Extended European Search Report mailed on Apr. 1, 2015, for EP Application No. 12 810 640.8, filed on Jul. 9, 2012, 8 pages.

Extended European Search Report mailed on Nov. 23, 2015, for EP Application No. 13 790 688.9, filed on May 14, 2013, 9 pages.

Extended European Search Report mailed on Nov. 17, 2015, for EP Application No. 13 790 449.6, filed on Jan. 10, 2013, 8 pages.

Final Office Action mailed on Feb. 12, 2016, for U.S. Appl. No. 13/544,664, filed Jul. 9, 2012, 9 pages.

Final Office Action mailed on Aug. 26, 2016, for U.S. Appl. No. 13/894,054, filed May 14, 2013, 7 pages.

Final Office Action mailed on Jul. 26, 2016, for U.S. Appl. No. 14/876,628, filed Oct. 6, 2015, 5 pages.

International Search Report mailed on Apr. 4, 2014, for PCT Application No. PCT/US2013/068576, filed on Nov. 5, 2013, 5 pages.

International Search Report mailed on Aug. 19, 2016, for PCT Application No. PCT/US2016/032560, filed on May 13, 2016, 2 pages.

International Search Report mailed on Sep. 17, 2012, for PCT Application No. PCT/US2012/045969, filed on Jul. 9, 2012, 2 pages.

International Search Report mailed on Sep. 24, 2013, for PCT Application No. PCT/US2013/040976, filed on May 14, 2013, 2 pages.

International Search Report mailed on Mar. 26, 2013, for PCT Application No. PCT/US2013/021075, filed on Jan. 10, 2013, 2 pages.

International Search Report mailed on Jul. 24, 2015, for PCT Application No. PCT/US2015/026036, filed on Apr. 15, 2015, 2 pages.

Kamiyoshihara, M. et al. (2008). "The Utility of an Autologous Blood Salvage System in Emergency Thoracotomy for a Hemothorax After Chest Trauma," Gen. Thorac. Cardiovasc. Surg. 56:222.

Non-Final Office Action mailed on Aug. 13, 2015, for U.S. Appl. No. 13/544,664, filed Jul. 9, 2012, 8 pages.

Non-Final Office Action mailed on Aug. 2, 2016, for U.S. Appl. No. 13/544,664, filed Jul. 9, 2012, 6 pages.

Non-Final Office Action mailed on May 9, 2014, for U.S. Appl. No. 13/544,679, filed Jul. 9, 2012, 7 pages.

Non-Final Office Action mailed on Mar. 30, 2016, for U.S. Appl. No. 13/894,054, filed May 14, 2013, 9 pages.

Non-Final Office Action mailed on Sep. 5, 2014, for U.S. Appl. No. 13/738,919, filed Jan. 10, 2013, 8 pages.

Non-Final Office Action mailed on Mar. 20, 2015, for U.S. Appl. No. 14/613,807, filed Feb. 4, 2015, 8 pages.

Non-Final Office Action mailed on Dec. 15, 2015, for U.S. Appl. No. 14/876,628, filed Oct. 6, 2015, 8 pages.

Notice of Allowance mailed on Feb. 17, 2015, for U.S. Appl. No. 14/072,625, filed Nov. 5, 2013, 10 pages.

Notice of Allowance mailed on May 12, 2014, for U.S. Appl. No. 13/544,646, filed Jul. 9, 2012, 10 pages.

Notice of Allowance mailed on Sep. 3, 2014, for U.S. Appl. No. 13/544,679, filed Jul. 9, 2012, 8 pages.

Notice of Allowance mailed on Nov. 10, 2014, for U.S. Appl. No. 13/738,919, filed Jan. 10, 2013, 10 pages.

Notice of Allowance mailed on Jun. 25, 2015, for U.S. Appl. No. 14/613,807, filed Feb. 4, 2015, 10 pages.

Sant et al. (2012). "Exsanguinated Blood Volume Estimation Using Fractal Analysis of Digital Images," Journal of Forensic Sciences 57:610-17.

Written Opinion of the International Searching Authority mailed on Apr. 4, 2014, for PCT Application No. PCT/US2013/068576, filed on Nov. 5, 2013, 6 pages.

Written Opinion of the International Searching Authority mailed on Aug. 19, 2016, for PCT Application No. PCT/US2016/032560, filed on May 13, 2016, 6 pages.

Written Opinion of the International Searching Authority mailed on Sep. 17, 2012, for PCT Application No. PCT/US2012/045969, filed on Jul. 9, 2012, 4 pages.

Written Opinion of the International Searching Authority mailed on Sep. 24, 2013, for PCT Application No. PCT/US2013/040976, filed on May 14, 2013, 4 pages.

Written Opinion of the International Searching Authority mailed on Mar. 26, 2013, for PCT Application No. PCT/US2013/021075, filed on Jan. 10, 2013, 6 pages.

Written Opinion of the International Searching Authority mailed on Jul. 24, 2015, for PCT Application No. PCT/US2015/026036, filed on Apr. 15, 2015, 6 pages.

U.S. Appl. No. 15/154,921, filed May 13, 2016, by Satish et al. (Copy not attached).

ACOG (2012). "Optimizing protocols in obstetrics," Series 2, 25 total pages.

Adkins, A.R. et al. (2014). "Accuracy of blood loss estimations among anesthesia providers," AANA J. 82(4):300-306.

Al-Kadri, H.M. et al. (2014). "Effect of education and clinical assessment on the accuracy of post partum blood loss estimation," BMC Preg. Childbirth 14:110, 7 total pages.

AWHONN Practice Brief (2014). "Quantification of blood loss: AWHONN practice brief number 1," AWHONN p. 1-3.

Bose, P. et al. (2006). "Improving the accuracy of estimated blood loss at obstetric haemorrhage using clinical reconstructions," BJORG 113(8):919-924.

Eipe, N. et al. (2006). "Perioperative blood loss assessment—How accurate?" Indian J. Anaesth. 50(1):35-38.

Habak, P.J. et al. (2016). "A comparison of visual estimate versus calculated estimate of blood loss at vaginal delivery," British J. Med. Medical Res. 11(4):1-7.

Holmes, A.A. (2014). "Clinical evaluation of a novel system for monitoring surgical hemoglobin loss," Anesth. Analg. 119(3):588-594.

Jones, R. (2015). "Quantitative measurement of blood loss during delivery," AWHONN p. S41.

Lyndon, A. et al. (2010). "Blood loss: Clinical techniques for ongoing quantitative measurement," CMQCC Obstetric Hemorrhage Toolkit, pp. 1-7.

Lyndon, A. et al. (2015). "Cumulative quantitative assessment of blood loss," CMQCC Obstetric Hemorrhage Toolkit Version 2.0, pp. 80-85.

Manikandan, D. et al. (2015). "Measurement of blood loss during adenotonsillectomy in children and factors affecting it," Case Reports in Clinical Medicine 4:151-156.

Merck for Mother's Program (2012). Blood loss measurement: Technology opportunity assessment, 9 total pages.

Roston, A.B. et al. (2012). "Chapter 9: Blood loss: Accuracy of visual estimation," in A comprehensive textbook of postpartum hemorrhage: An essential clinical reference for effective management, $2^{nd}$ edition, Sapiens publishing, pp. 71-72.

(56) References Cited

OTHER PUBLICATIONS

Schorn, M.N. (2010). "Measurement of blood loss: Review of the literature," *J. Midwifery and Women's Health* 55(1):20-27.
Sukprasert, M. et al. (2006). "Increase accuracy of visual estimation of blood loss from education programme," *J. Med. Assoc. Thai* 89(suppl. 4):S54-S59.
Notice of Allowance mailed on Feb. 15, 2017, for U.S. Appl. No. 13/544,664, filed Jul. 9, 2012, 10 pages.

\* cited by examiner

METHOD FOR SETTING A BLOOD TRANSFUSION PARAMETER

CROSS-REFERENCE TO RELATED APPLICATIONS

This application claims the benefit of U.S. Provisional Application No. 61/722,780, filed on Nov. 5, 2012, which is incorporated in its entirety by this reference.

The application is related to U.S. patent application Ser. No. 13/894,054, filed on May 14, 2013, which claims the benefit of U.S. Provisional Patent Application No. 61/776,577, filed on Mar. 11, 2013, U.S. Provisional Patent Application No. 61/646,822, filed on May 14, 2012, U.S. Provisional Patent Application No. 61/703,179, filed on Sep. 19, 2012, and U.S. Provisional Patent Application No. 61/722,780, filed on Nov. 5, 2012, all of which are incorporated herein in their entireties by this reference.

The application is also related to U.S. patent application Ser. No. 13/544,646, filed on Jul. 9, 2012 which claims the benefit of U.S. Provisional Patent Application No. 61/506,082, filed Jul. 9, 2011, U.S. Provisional Patent Application Ser. No. 61/646,818, filed May 14, 2012, and U.S. Provisional Patent Application Ser. No. 61/646,822, filed May 14, 2012, all of which are incorporated herein in their entireties by this reference.

The application is further related to U.S. patent application Ser. No. 13/738,919, filed on Jan. 10, 2013, which claims the benefit of U.S. Provisional Application No. 61/703,179, filed on Sep. 19, 2012, U.S. Provisional Patent Application No. 61/646,822, filed on May 12, 2012, and U.S. Provisional Patent Application No. 61/722,780, filed on Nov. 5, 2012, all of which are incorporated in their entireties by this reference.

TECHNICAL FIELD

This invention relates generally to the surgical field, and more specifically to a new and useful method for triggering blood cell salvage in the surgical field.

DESCRIPTION OF THE PREFERRED EMBODIMENTS

The following description of the preferred embodiment of the invention is not intended to limit the invention to these preferred embodiments, but rather to enable any person skilled in the art to make and use this invention.

1. First Method

Figure 1:
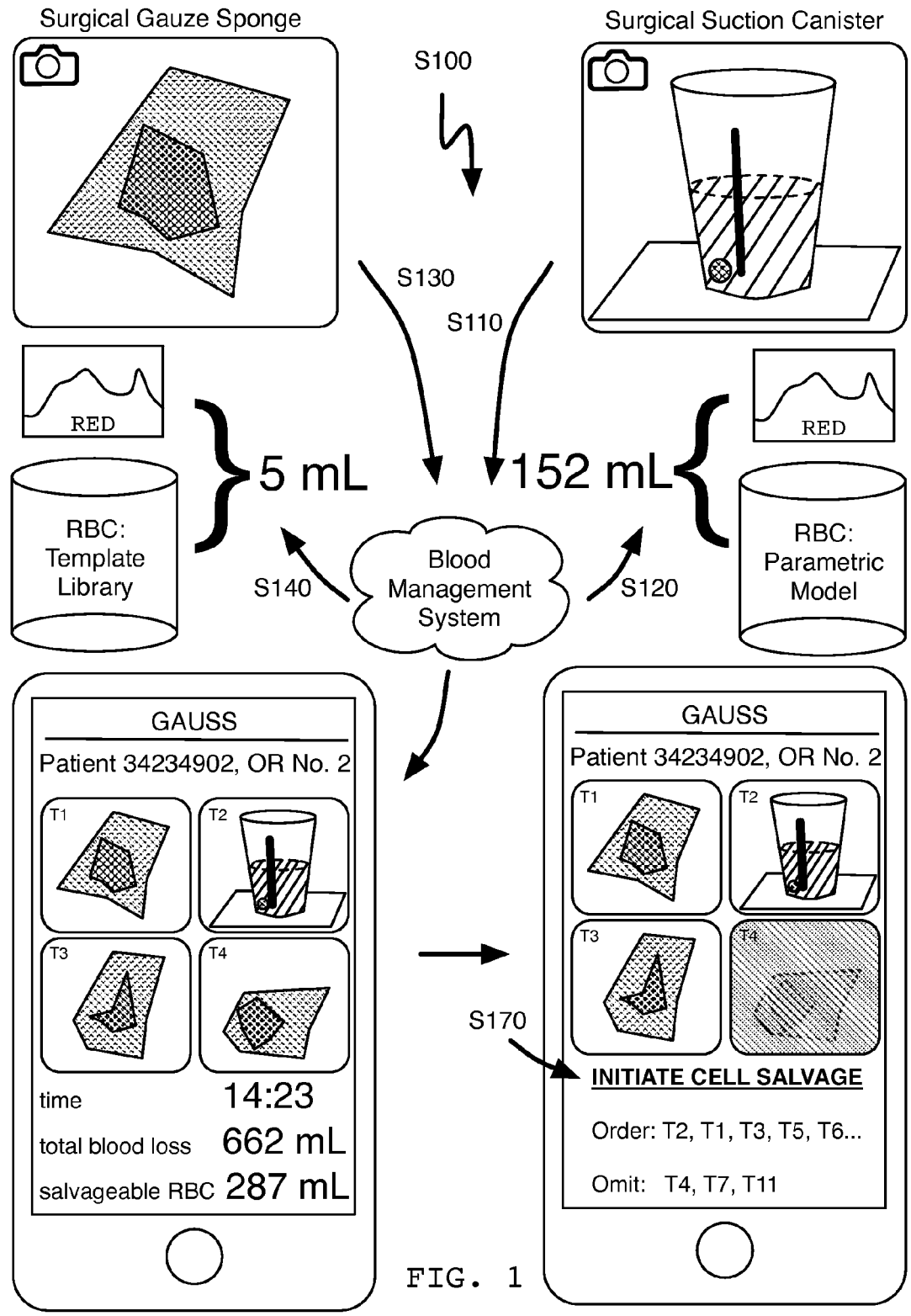
FIG. 1 is a flowchart representation of a first method of one embodiment of the invention.

As shown in FIG. 1, first method S100 for triggering blood cell salvage for a patient includes: processing a first photographic image of a canister to estimate a content of a blood component within the canister in Block S120; processing a second photographic image of a gauze sponge to estimate a content of the blood component in the gauze sponge in Block S140; estimating an aggregate salvageable blood component content for the patient based on the estimated content of the blood component within the canister and the estimated content of the blood component in the gauze sponge in Block S150; in response to the estimated aggregate salvageable blood component content exceeding a threshold salvageable blood component content, generating a prompt to salvage the blood component from fluid within the canister and from the gauze sponge in Block S170.

First method S100 functions to estimate an amount of blood collected in a canister, a gauze sponge, or other container or surface, to estimate an amount of a blood component (e.g., red blood cells) that can be salvaged from the collected blood, and to trigger or prompt blood cell salvage from the canister, the gauze sponge, and/or the other container or surface based on a patient's current blood transfusion need, a predicted future blood transfusion need of the patient, and/or a blood cell salvage cost. Generally, first method S100 implements machine vision techniques to analyze images of surgical gauze sponges and a surgical canister, such as described in U.S. patent application Ser. No. 13/544,646 and U.S. patent application Ser. No. 13/738,919, filed on Jul. 9, 2012 and Jan. 10, 2013, respectively, which are incorporated herein in their entireties by this reference. First method S100 can additionally or alternatively process images of an other bloodied media, such as surgical towels, clothing, surgical dressings, surgical tools, surgical drapes, peripartum under-buttocks drapes, catheter (e.g., Foley) bags, surgical irrigation bags, or a floor, table, or other surface within a hospital operating room, etc.

First method S100 can implement patient circulatory status prediction techniques, such as described in U.S. patent application Ser. No. 13/894,054, filed on May 14, 2013, which is also incorporated herein in its entirety by this reference, to determine when the patient is in need of a blood transfusion or a particular blood component (e.g., red blood cells, plasma) and prompt or trigger blood cell salvage accordingly. First method S100 can additionally or alternatively access a database specifying blood cell salvage parameters and costs (e.g., cell salvage technician, disposables, transfusion, transfusable blood inventory, and insurance costs) to prompt or trigger cell salvage from a surgical canister, a gauze sponge, etc. when such cell salvage becomes financially feasible or responsible. First method S100 can also factor in risk and corresponding costs associated with allogeneic and autologous blood transfusion in assessing cell salvage cost. Once first method S100 determines that the patient is in need of a blood transfusion and/or that a suitable salvageable blood volume is available to surpass a cell salvage cost threshold, first method S100 can trigger an alarm to initiate blood cell salvage, transmit a cell salvage notification to a cell salvage technician, anesthesiologist, surgeon, etc., or prompt blood cell salvage for autologous transfusion in any other suitable way.

First method S100 can therefore be applicable to surgical scenarios in which a patient experiences blood loss and in which the patient's blood is collected, such as with surgical gauze sponges, surgical towels, surgical suction canisters, catheters, and/or surgical drapes, etc. Generally, once a fluid containing blood is collected, blood and/or components of the blood can be extracted from the fluid through an interoperative blood salvage technique or apparatus. For example, as shown in FIG. 2A, a centrifugal blood salvage machine can separate components of the collected fluid by weight, such as by separating red blood cells, plasma (and free hemoglobin), and waste based on the density of each. Once a patient transfusion need is identified or predicted (e.g., in Block S160 described below), first method S100 can prompt or trigger cell salvage of one or more particular blood components for transfusion back into the patient.

First method S100 can be implemented by a computer system, such as a cloud-based computer (e.g., Amazon EC2), a mainframe computer system, a grid-computer system, or any other suitable computer system. Some or all of the Blocks of first method S100 can be implemented by a mobile computing device statically or dynamically arranged within an operating room, such as a tablet or a smartphone incorporating a camera or other optical sensor. Blocks of first method S100 can also be accessible through a web browser and/or through a native application executing on any other computing device, such as a laptop computer, a desktop computer, a tablet, a smartphone, a personal data assistant (PDA), a personal music player, etc. Additionally or alternatively, Blocks of first method S100 can be implemented remotely. For example, image processing within first method S100 can be implemented on a remote server or over a distributed network of computing devices, and blood component content estimate results can be transmitted from the remote server back to a computing device (e.g., a tablet) with the operating room. The computer system can further interface with local or remote databases, such as a patient medical record or medical history database, a health insurance database, a blood bank or blood inventory database, or a blood salvage technician or technical support database. The computer system can also communicate messages and/or notifications to relevant users or entities. For example, first method S100 can distribute a notification to begin blood salvage to a blood salvage technician outside of an operating room through an email, SMS text message, or in-application notification on a mobile phone or tablet assigned to and carried by the cell salvage technician. First method S100 can further communicate a visual alarm to begin transfusion (e.g., to an anesthesiologist) through a display on a tablet arranged within the operating room. However, first method S100 can be implemented by any another computer system and can communicate blood-related data with one or more users and/or entities in any other suitable way.

1.1 Images

As shown in FIG. 4A, one variation of first method S100 includes Block S110, which recites, with an optical sensor, capturing an image of a canister containing a fluid. This variation of first method S100 can similarly include Block S130, which recites, with an optical sensor, capturing an image of a gauze sponge including an absorbed fluid, as shown in FIG. 3A. Generally, Block S110 and Block S130 function to collect images of a suction canister and one or more surgical gauze sponges and to pass these images to Block S120 and Block S140, respectively. In one implementation, the images collected in Blocks S110 and S130 are digital photographic images in color (e.g., with red, green, and blue color components). However, Blocks S110 and S130 can collect any other suitable type of image.

Block S110 and/or Block S130 can interface with a standalone optical sensor arranged within an operating room to capture images of the canister and the gauze sponge. For example, the optical sensor can be a camera coupled to a fluid collection system including the suction canister. In another example, the optical sensor can be a camera mounted overhead an operating table.

Figure 4:
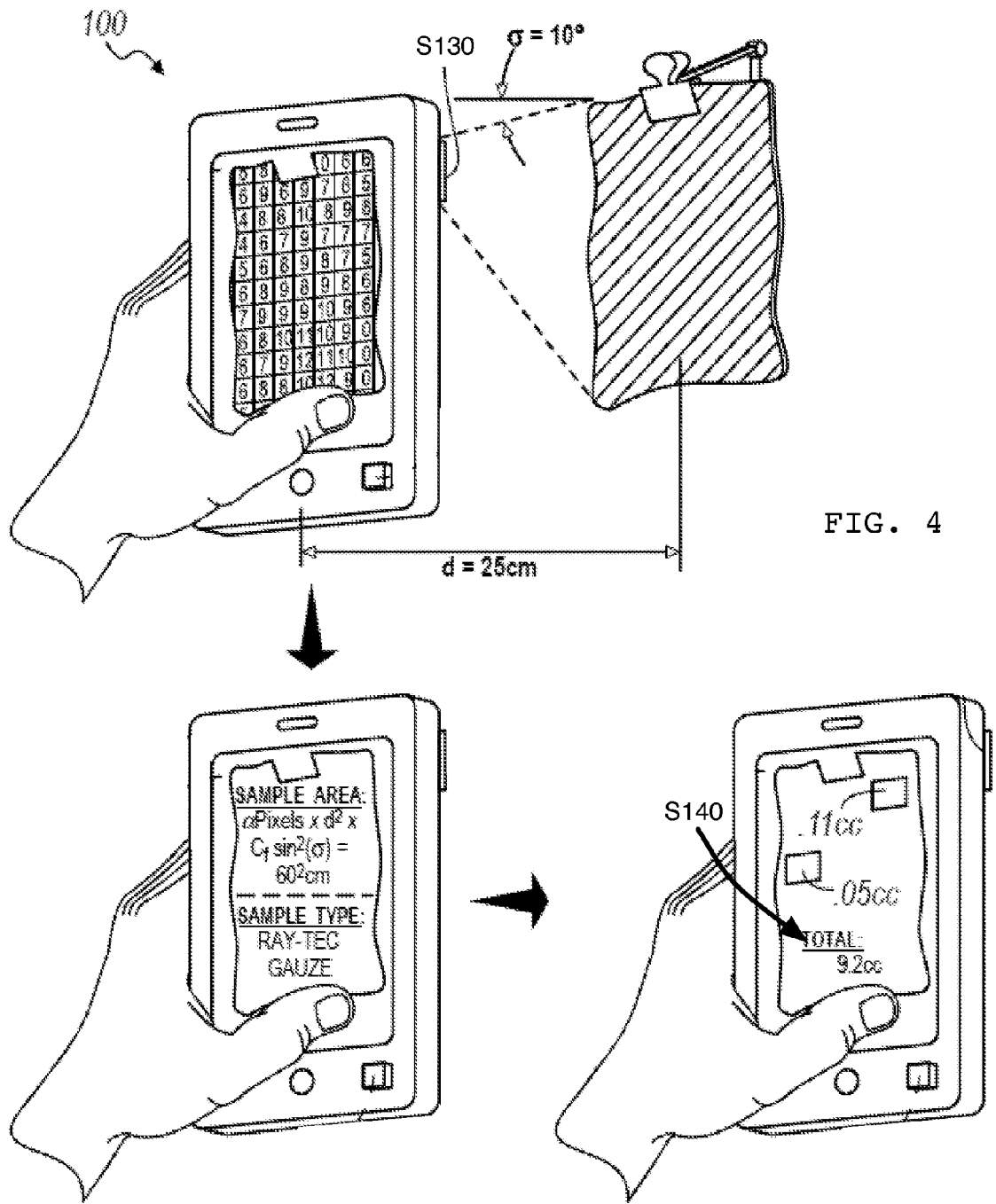
FIG. 4 is a flowchart representation of one variation of the first method.

Alternatively, Block S110 and/or Block S130 can interface with an optical sensor that is a camera integrated into a smartphone, tablet, or other mobile computing device, such as shown in FIG. 4. In this implementation, an anesthesiologist, surgeon, nurse, technician, or other user within the operating room can manipulate the computing device within the operating room to image various bloodied elements therein, such as a gauze sponge, a surgical towel, a suction or cell salvage canister, a blood transfusion bag, and a surgical drape.

Block S110 and Block S130 can also interface with multiple distinct optical sensors, arranged within the operating room, that cooperate to capture images of various surgical or surgery-related objects or surfaces. For example, Block S110 can capture or retrieve the image of the canister from a camera integrated in a tablet coupled to a fluid collection system including the canister, and Block S130 can capture the image of the gauze sponge through a camera integrated into a second tablet arranged over a surgical gauze tracking and storage table, wherein the first and second tablets transmit images, over the Internet, to a remote server that implements Block S120 and Block S140 of first method S100.

Block S110 can capture images of the canister according to a time schedules, such as every thirty seconds or every two minutes during a surgery. Block S110 can alternatively capture images of the canister according to a manual input, such as from a nurse or anesthesiologist. Block S110 can also implement machine vision and object recognition techniques to identify the canister within the field of view of the optical sensor, wherein, once Block S110 and Block S120 identify a suitable bloodied item within the field of view, Block S110 triggers capture of the image of the canister. By determining the quantity and/or content of fluid within the canister in Block S120, first method S100 can thus track fluid collection in the canister over time, which can be useful in tracking trends in fluid loss and predicting future fluid loss or a patient, such as described in U.S. patent application Ser. No. 13/894,054.

Block S130 can similarly capture images of gauze sponges over time to create of library of images of surgical gauze sponges used throughout a surgery, such as described in U.S. patent application Ser. No. 13/544,646. Like Block S110, Block S130 can implement machine vision and/or object recognition techniques to trigger capture of an image of a gauze sponge with a camera or other optical sensor. Alternatively, Block S130 can capture the image of the gauze sponge according to a manual input or according to any other trigger. By estimating blood content in surgical gauze sponges over time in Block S140, first method S100 can thus track blood content in multiple gauze sponges over time, which can indicate a rate of gauze sponge use over time (i.e., throughout the surgery), enable identification of trends in patient fluid (e.g., blood) loss over time, and support prediction of future fluid loss and fluid needs of the patient.

Block S110 and Block S130 can be implemented locally on a computing device incorporating one or more optical sensors (e.g., a smartphone or tablet) or connected to one or more optical sensors (e.g., a laptop or desktop computer) to trigger image capture and to the collect captured images before passing these images to Blocks S120 and S140, respectively. Alternatively, Blocks S110 and S130 can be implemented remotely, such as on a remote server, to remotely trigger image capture and/or collect images captured by one or more local optical sensors.

Though Blocks S110 and S130 are described as collecting images of a canister and a gauze sponge, respectively, Blocks S110 and S130 can generally be described as capturing an image of a first substrate and an image of the second substrate, respectively, wherein the first substrate and the second substrate can be any of a cell-salvage reservoir (i.e., canister) a gauze sponge, a suction canister, a surgical towel, a surgical drape, or any other bloodied item within the field of view of one or more optical sensors within an operating room. However, Block S110 and Block S130 can function in any other way to capture and/or collect images of bloodied items for processing in subsequent Blocks of first method S100 described below.

1.2 Image Processing

As shown in FIG. 4B, Block S120 of first method S100 recites processing a first photographic image of a canister to estimate a content of a blood component within the canister in Block S120. (Block S120 can similarly recite processing an image of a first substrate to estimate a content of a blood component within the first substrate). Generally, Block S120 functions to analyze color properties of pixels in one or more regions corresponding to the canister in the first image to estimate a volume, mass, weight, (volumetric, weight, or mass) concentration, or other metric of the quantity of total blood, red blood cells, in-cell hemoglobin, free hemoglobin, white blood cells, plasma, and/or other blood component within the canister.

As described in U.S. patent application Ser. No. 13/738, 919, Block S120 can implement one or more machine vision techniques paired with a parametric and/or non-parametric model to estimate the quantity and quality of fluid within a fluid canister. In one implementation, Block S110 extracts a redness value from an area of an image of the canister and correlates the redness value with a red blood cell and/or hemoglobin content or concentration through a parametric model. In another implementation, Block S120 matches an area of an image of a canister with a template image of known red blood cell and/or hemoglobin content or concentration.

Block S120 can also identify a fluid meniscus in the image of the canister and correlate the level of the meniscus with a fluid volume, such as by accessing a lookup table for the particular type of canister identified within the image. From the estimate fluid volume and the estimated red blood cell and/or hemoglobin concentration within the canister, Block S120 can thus determine the amount of hemoglobin and/or red blood cells (e.g., a fluid quality) within the canister. From this Block S120 can estimate the total volume of blood within the fluid canister at any given time. Block S120 can also implement similar techniques to identify other contents of the fluid within the canister, such as bile, saliva, gastric fluid, mucus, pleural fluid, saline, or fecal matter.

Figure 3:
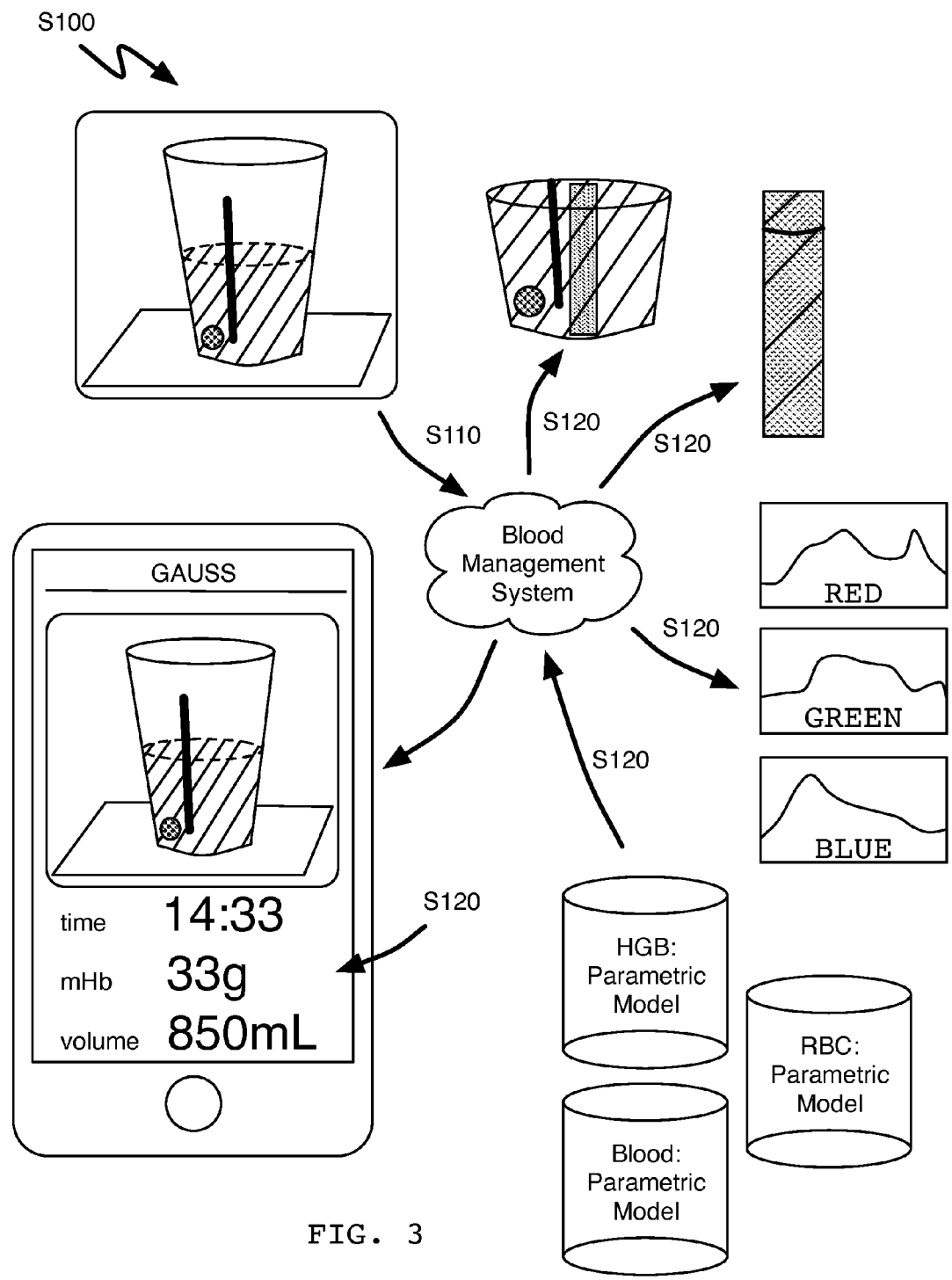
FIG. 3 is a flowchart representation of one variation of the first method.

In one implementation, Block S120 identifies, within the first photographic image, a reference marker on the canister, selects an area of the first photographic image based on the reference marker, correlates a portion of the selected area with a fluid level within the canister, and estimates a volume of fluid within the canister based on the fluid level, such as based on a known type or size of the canister, as shown in FIG. 3. Block S120 then extracts a feature from the selected area, correlates the extracted featured with a concentration of the blood component within the canister, and estimates a quantity of the blood component within the canister based on the estimated volume and the concentration of the blood component within the canister. For example, Block S120 can extract a redness value from the selected area and correlating the redness value with a quantity (e.g., volume or mass) of red blood cells and/or hemoglobin within the canister, such as described in U.S. patent application Ser. No. 13/738,919.

Figure 5A:
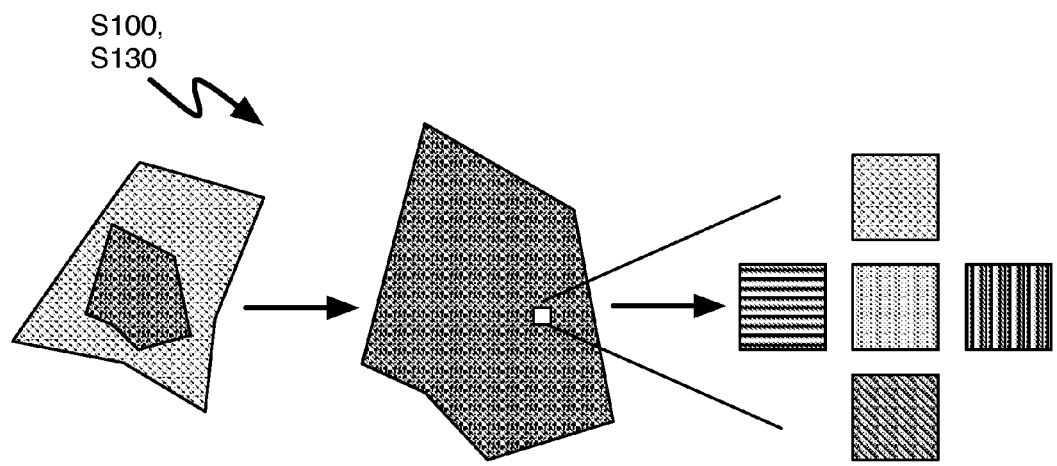
FIGS. 5A and 5B are a flowchart representations of one variation of the first method.
Figure 5B:
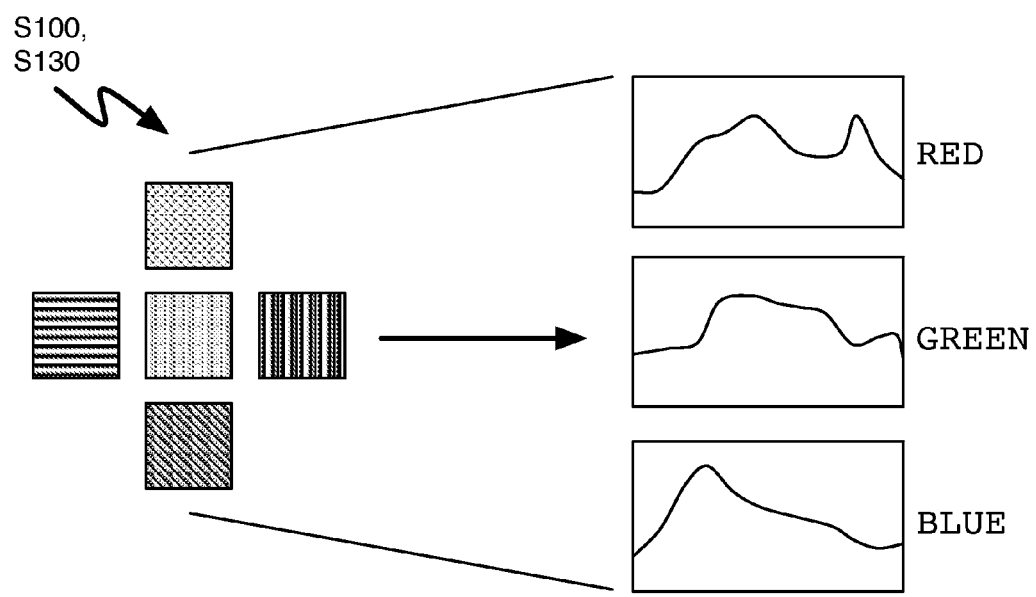

In addition to estimating a blood component content in the canister, Block S120 can also detect and/or estimate an amount of other substances in the canister. For example, Block S120 can extract color values in the red, green, and blue color spaces from a set of pixels in the first image corresponding to the canister, as shown in FIGS. 5A and 5B. Block S120 can then correlate a combination of color values in various color spaces with the presence of another substance, such as bile, saliva, gastric fluid, mucus, pleural fluid, saline, or fecal matter, in the canister. If a fouling substance, such as fecal matter, is detected in the canister, Block S120 can flag the canister as fouled and therefore unsuitable for cell salvage for autologous blood transfusion. Once the canister is flagged in Block S120, Block S150 can thus exclude an estimate blood component content in the canister from the aggregate salvageable blood component content (until the canister is replaced or emptied, rinsed, and disinfected).

Block S120 can also timestamp subsequent images of the canister to enable volumetric and/or content tracking of the canister over time as the canister is filled, replaced, and/or emptied. First method S100 can further correlate changes in fluid level within the canister (and fluid content of the gauze sponges) with total patient fluid (e.g., blood) loss, as described in U.S. patent application Ser. No. 13/894,054, and Block S170 can apply this metric to prompt blood component salvage, as described below. However, Block S120 can function in any other way to determine the quality and/or quantity of contents of the fluid canister.

As shown in FIG. 3B, Block S140 of first method S100 recites processing a second photographic image of a gauze sponge to estimate a content of the blood component in the gauze sponge. (Block S140 can alternatively recite processing an image of a second substrate to estimate a content of the blood component within the second substrate.) Generally, Block S140 functions to analyze color properties of pixels in one or more regions corresponding to the gauze sponge in the second image to estimate a volume, mass, weight, (volumetric, weight, or mass) concentration, or other metric of the quantity of total blood, red blood cells, in-cell hemoglobin, free hemoglobin, white blood cells, plasma, and/or other blood component within the sponge gauze.

As described in U.S. patent application Ser. No. 13/544, 646, Block S140 can implement one or more machine vision techniques to estimate the quantity and quality of fluid within one or more surgical gauze sponges, surgical towels, surgical dressings, etc. Like Block S120, Block S140 can implement a parametric model and/or a non-parametric model to estimate the quantity of hemoglobin, red blood cells, or other blood component within the gauze sponge shown in the second image.

For example, Block S140 can process the second photographic image by extracting a feature from a portion of the second photographic image corresponding to the gauze sponge, tagging the portion of the second photographic image with a blood volume indicator according to the extracted feature, estimating an extracorporeal blood volume in the portion the gauze sponge based on the blood volume indicator, and estimating the content of the blood component in the gauze sponge based on the estimated extracorporeal blood volume and an estimated hematocrit of the patient, as described in U.S. patent application Ser. No. 13/544,646 and shown in FIG. 4.

Block S140 can also flag, prioritize, and/or order particular sponges for blood component salvaging. In particular, Block S140 can implement image processing techniques to estimate a content of a blood component in each of a set of gauze sponges over time (e.g., during a surgery) and tag each with a priority or order for cell salvage based on an estimated salvageable blood component from each gauze sponge in the set with gauze sponges with higher estimated salvageable content tagged with higher priority than gauze sponges with lower estimate salvageable blood content. As additional images of additional gauze sponges are processed, Block S140 can update priority or order tags from previous gauze sponges accordingly. In one example, Block S140 can process a photographic image to determine that a corresponding first gauze sponge includes 50 mL of absorbed blood and thus flag this sponge as a suitable candidate from which to efficiently salvage plasma, red blood cells, or complete blood. In this example, Block S140 can then process a subsequent photographic image to determine that a corresponding second gauze sponge includes only 5 mL of absorbed blood. Block S140 can thus identify the second sponge as a lesser candidate for blood component salvaging and prioritize the first sponge gauze for cell salvage over the second gauze sponge or prompt a technician, nurse, anesthesiologist, etc. to discard the second gauze sponge altogether. In this example, by prioritizing the first gauze sponge over the second gauze sponge—or removing the second gauze sponge from cell salvage altogether—Block S140 can enable substantially efficient selection of gauze sponges for blood component salvaging.

When flagging a gauze sponge for cell salvage, Block S140 can display a visual cue on a tablet or other mobile computer device as a user (e.g., a nurse, anesthesiologist, cell salvage technician, etc.) holds a sponge in front of the optical sensor (within the mobile computing device) for imaging (e.g., in Block S120). Block S140 can also trigger an audible alarm or any other cue to signal to the user to set a suitable gauze sponge aside for subsequent salvaging and/or to discard a particular gauze sponge. Block S140 can also rank surgical gauze sponges according to an estimated salvage amount from each sponge and display this information to the user, such as substantially in real-time and/or substantially immediately after a gauze sponge is imaged. For example, Block S140 can prompt a user, such as through a visual display, to arrange subsequent sponges across a counter or tray in order of estimated blood content. Alternatively, Block S140 can prompt the user to manually tag each sponge with an estimated blood volume or estimated blood volume rank, such as with a pen or plastic crimp tag. Yet alternatively, Block S140 can prompt a user to set each imaged sponge in a particular "bucket" associated with a range of estimated blood volumes. For example, Block S140 can prompt a user to place an analyzed sponge in one of a 0-10 mL bucket, a 10-20 mL bucket, and 30-40 mL bucket, a 40-50 mL bucket, and a >50 mL bucket. In this example, once Block S170 triggers this alarm for blood component salvaging, Block S170 can first prompt a user to begin blood salvage from the >50 mL bucket, followed by the 40-50 mL bucket, followed by the 30-40 mL bucket, and so on, such as according to changes in the patient's fluid and/or blood transfusion needs over time (e.g., during a surgery).

Block S140 can also flag certain sponges as inappropriate for blood recovery. Like Block S120, in addition to estimating a volume and quantity of blood in a gauze sponge, Block S140 can implement one or more color features extracted from the second image to determine or estimate the content of other substances within the gauze sponge, such as bile, saliva, gastric fluid, mucus, pleural fluid, saline, or fecal matter. Like Block S120, Block S140 can also flag a gauze sponge for exclusion from cell salvage given detected presence of a fouling substance on or within the gauze sponge. For example, if Block S140 determines the presence of fecal matter on a particular gauze sponge, Block S140 can issue a flag, such as in real-time as a user is holding the sponge in from of the camera, and advise the user to quarantine the sponge away from other sponges allocated for blood component salvage.

Block S140 can also implement a sponge counter, time stamp images of each gauze sponge, and store images of gauze sponges to prevent double counting of sponges and sponge contents, and handle extracted data pertaining to various images gauze sponges in any other way, such as described in U.S. patent application Ser. No. 13/544,646. However, Block S140 can function in any other way to process the image of the sponge—and additional images of additional sponges—to estimate a content (e.g., volume) and/or quality of blood in the sponge.

In one implementation, Block S120 estimates the quantity (e.g., mass, volume) of blood component (e.g., red blood cells, hemoglobin, etc.) in the canister by: receiving a first quantity of a volume of fluid dispensed from a canister onto the first substrate comprising a gauze sponge; extracting a feature from a portion of the image corresponding to the gauze sponge; tagging the portion of the image with a blood volume indicator according to the extracted feature; calculating a blood component concentration in the gauze sponge based on the blood volume indicator and the first quantity; associating the blood component concentration in the gauze sponge with a blood component concentration within the canister; and estimating a salvageable blood component content within the canister based on a volume of fluid within the canister and the blood component concentration within the canister.

Generally, in the foregoing implementation, Block S120 implements methods or techniques of Block S140 to estimate a blood component concentration within gauze sponge once a known volume of fluid is deposited from the canister onto the gauze sponge. (This volume can be preset or prescribed, or this volume can be entered manually by a user, such as into a tablet or smartphone executing the method.) Block S120 can then correlate the concentration of the blood component within the gauze sponge with a concentration of the blood component within the canister and finally apply a volume of fluid within the canister to the associated concentration of the blood component within the canister to estimate the total blood component quantity within the canister. For example, a user (e.g., a nurse, an anesthesiologist) can aspirate a known volume of bloody fluid (e.g., bloodied saline) from a blood-bearing container (e.g., a waste wall suction canister or a reservoir within a cell salvage system) into a 30 mL aliquot through the sampling port and then pour the known volume of fluid from the aliquot onto a gauze sponge. The methods and techniques of Block S140 can then be applied to an image of the gauze sponge to estimate a blood component indicator (e.g., hemoglobin mass) in the gauze sponge. By combining this estimate of the blood component indicator of the gauze sponge with the known volume of fluid dispensed onto the gauze sponge, Block S120 can estimate the blood indicator concentration (e.g., hemoglobin concentration) of the sanguineous fluid deposited from the container onto the gauze sponge. The blood component content within the container is then calculated by combining the remaining existing volume of fluid within the container with the estimate the blood indicator concentration of the fluid. Block S120 can therefore estimate a blood component content of the canister by processing an image of an other substrate that includes a known volume of fluid deposited from the container onto the substrate. However, Block S120 can function in any other way to estimate a blood component content within the canister.

1.3 Aggregate Salvageable Blood Component

Block S150 of first method S100 recites estimating an aggregate salvageable blood component content for the patient based on the estimated content of the blood component within the canister and the estimated content of the blood component in the gauze sponge. (Block S150 can similarly recite estimating an aggregate salvageable blood component content for the patient based on the estimated content of the blood component within the first substrate and the estimated content of the blood component within the second substrate.) Generally, Block S150 functions to estimate an amount of red blood cells, plasma, hemoglobin, or other blood component that can be salvaged from fluids in two or more bloodied substrates, such as from fluid contained in the canister and from fluid absorbed into a gauze sponge.

In one implementation, Block S150 combines estimated blood component contents (e.g., volume, mass, or weight, etc.) in various sponges into an aggregated blood component content and then apply known or predicted blood extraction inefficiencies to the aggregated blood component content to estimate the aggregate salvageable blood component content from the various substrates. Because centrifugal blood salvage machines can damage red blood cells during a fluid separation process, blood component salvage can yield less than 100% of blood components from a sample of blood-containing fluid. For example, certain centrifuge speeds and times required to adequately separate red blood cells from collected fluids can cause a certain percentage (e.g., ~5%) of the separated red blood cells to lyse, split, or disintegrate, thereby becoming useless to a patient (and even detrimental if transfused back into the patient). In this example, Block S150 can thus apply a static predicted loss percentage to the aggregated blood component content for the various substrates to generate the aggregate salvageable blood component estimate.

Furthermore, fluid absorbed into a gauze sponge is often collected by soaking the sponge in saline solution; the gauze sponge is eventually wrung into the saline solution, and the remaining solution is then dispensed into a cell salvage machine for separation of blood component, saline, and other substances in the solution. Even with repeated wringing, this process does not always yield complete recovery of a blood component (e.g., red blood cells) from the sponge. Furthermore, blood component loss from initial extraction of the blood component from a gauze sponge can therefore differ across different gauze sponge types (and surgical towel types, etc.). Blood component loss from initial fluid extraction from the gauze sponge can also differ from fluid extraction from the canister, which can be emptied directly into the cell salvage machine and rinsed to load nearly all (e.g., >99%) of the blood component from the canister into the cell salvage machine. Block S150 can therefore account for fluid extraction inefficiencies from the various substrates, such as by applying different extraction efficiencies for blood component salvage from each type of gauze sponge, surgical towel, canister, etc.

To estimate the total amount of salvageable blood component(s) from various substrates, Block S150 can also access or retrieve various data collected in Block S120 and S140. For example, Block S150 can implement any of a total fluid volume within the canister, an estimated blood volume within the canister, an estimated blood volume in one or more gauze sponges, an estimated hematocrit of blood in one or more substrates, an estimated average hematocrit of blood in the canister, saline, blood, or other intravenous fluid infusions of the patient during the surgery, etc. to estimate a volume, mass, or other quantitative measure of recoverable blood component from the fluid canister, the gauze sponge, and any other number and type or substrate.

Block S150 can further access data pertaining to the type of surgery, a surgical history of an operating surgeon and/or present anesthesiologist, a patient medical record, or any other relevant information pertaining to operating staff, the surgery, or the patient. Block S150 can then implement such data to predict a future blood component content in the canister, a future number of bloodied gauze sponges with corresponding blood component contents, and thus a future salvageable blood component yield from various future substrates.

Block S150 can also account for the presence of other fluids and/or matter identified in the gauze sponge and/or canister in Block S140 and Block S120, respectively. For example, if Block S120 determines that the canister includes fecal matter, Block S150 can exclude contents of the canister from the estimated total blood recovery. Block S150 can therefore cooperate with Blocks S120 and S140 determine if the contents of a canister or gauze sponge are safe for blood recovery in light of their contents as identified in Block S120 and Block S140, respectively.

Block S150 can also display the estimated aggregate salvageable blood component content on a display of a computing device (e.g., a tablet) within the operating room, such as substantially in real-time as Block S100 captures an image of the canister and Block S120 estimates a blood component content within the canister and/or as Block S130 captures an image of a gauze sponge and Block S140 estimates a blood component content within the gauze sponge. However, Block S150 can function in any other way to estimate an aggregate amount of a blood component salvageable from the canister, from the sponge, and/or from any number and type of bloodied substrates.

1.4 Patient Transfusion Need

Figure 6:
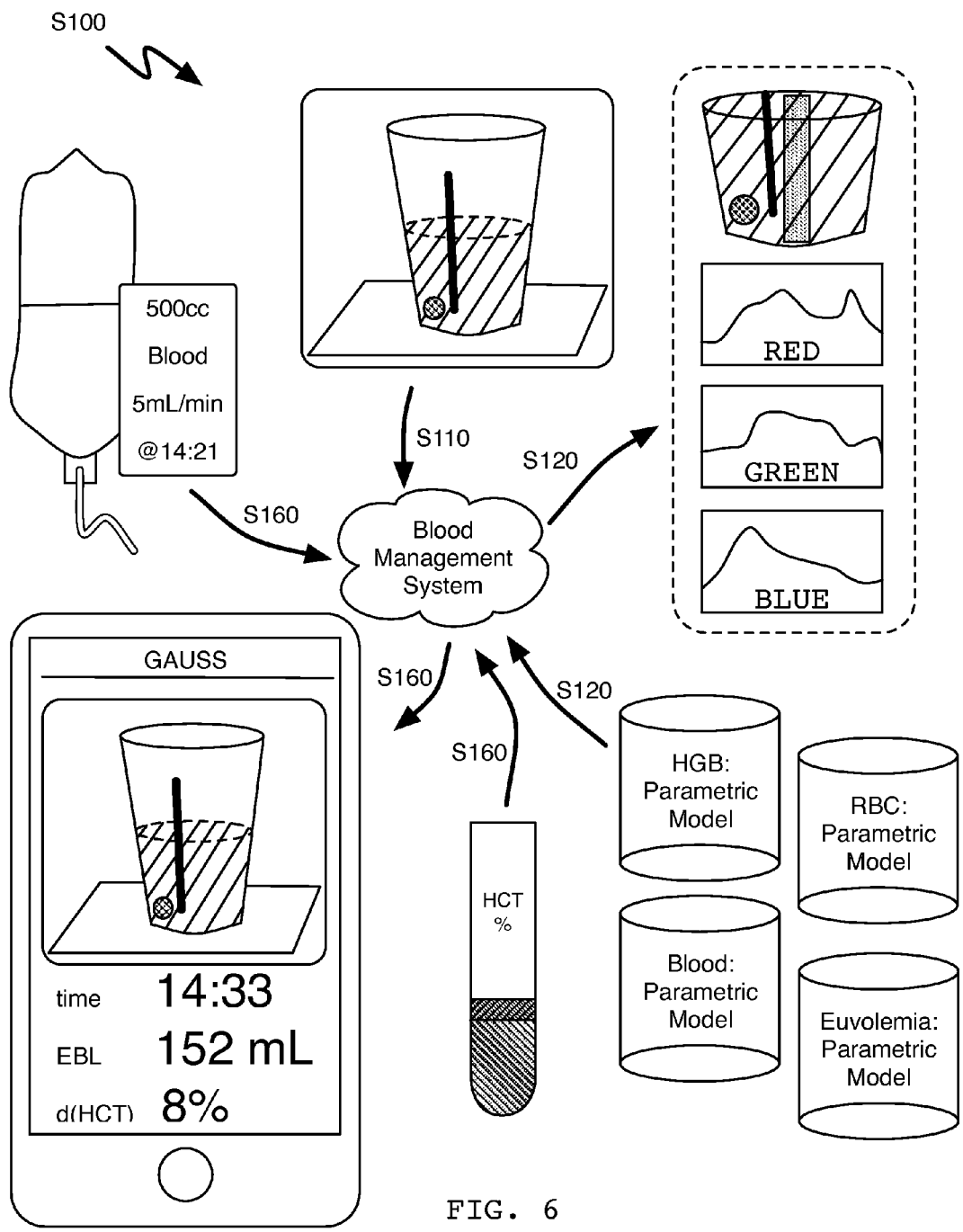
FIG. 6 is a flowchart representation of one variation of the first method.

As shown in FIG. 6, one variation of first method S100 includes Block S160, which recites predicting a patient transfusion need. Generally, Block S160 functions to estimate the quantity and quality of blood within the patient's circulatory system and to predict a future transfusion need of the patient accordingly based on a trend in blood loss of the patient over time. In particular, Block S160 can predict a current patient transfusion need and pass this predicted need to Block S170 to trigger immediate cell salvage for autologous blood transfusion. Block S160 can additionally or alternatively predict a future patient transfusion need based on patient blood loss trends and pass this predicted future need to Blocks S120, S140, and/or S150, etc. to guide a user (e.g., a cell salvage technician, a nurse, and anesthesiologist, etc.) in preparing bloodied substrates for initial blood extraction and subsequent blood component separation.

Figure 7A:
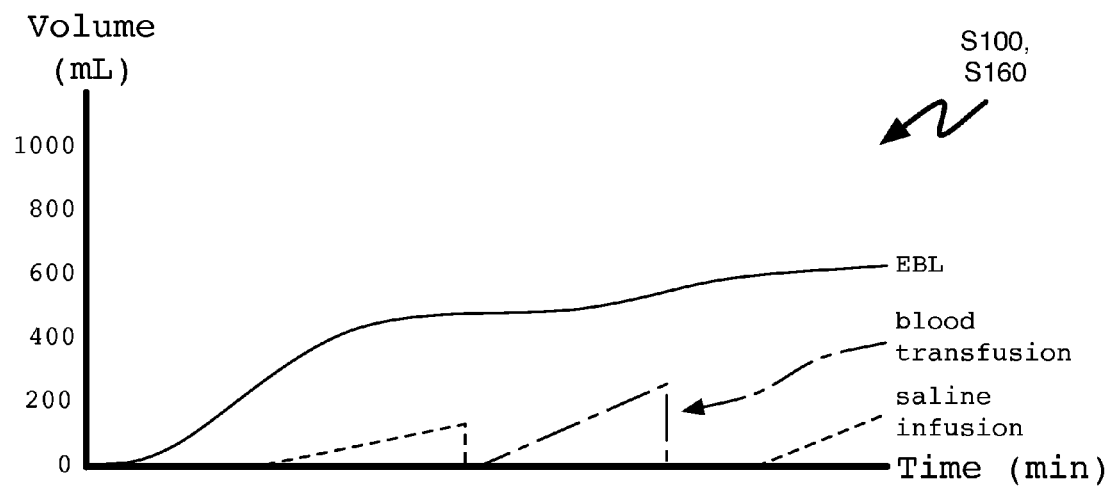
FIGS. 7A and 7B are graphical representations of variations of the first method.

As described in U.S. patent application Ser. No. 13/894, 054 and shown in FIGS. 7A and 9, Block S160 can estimate total patient blood loss over time by tracking estimated blood contents in the canister and various blood gauzes over time (or another combination of substrates). Block S160 can similarly track red blood cell loss, hemoglobin loss, and other intracorporeal fluid losses of the patient over time based on substrate contents extrapolated from images processed in Block S120 and S140. Block S160 can then compare the estimated patient blood loss to a threshold patient blood loss—such as based on patient age, gender, and weight—to identify a patient transfusion need. Block S160 can similarly extrapolate a trend in patient blood loss based on timestamps of various images of the canister and/or gauze sponges and corresponding blood contents to predict a future time at which the patient's total blood loss will surpass the threshold maximum blood loss.

Figure 7B:
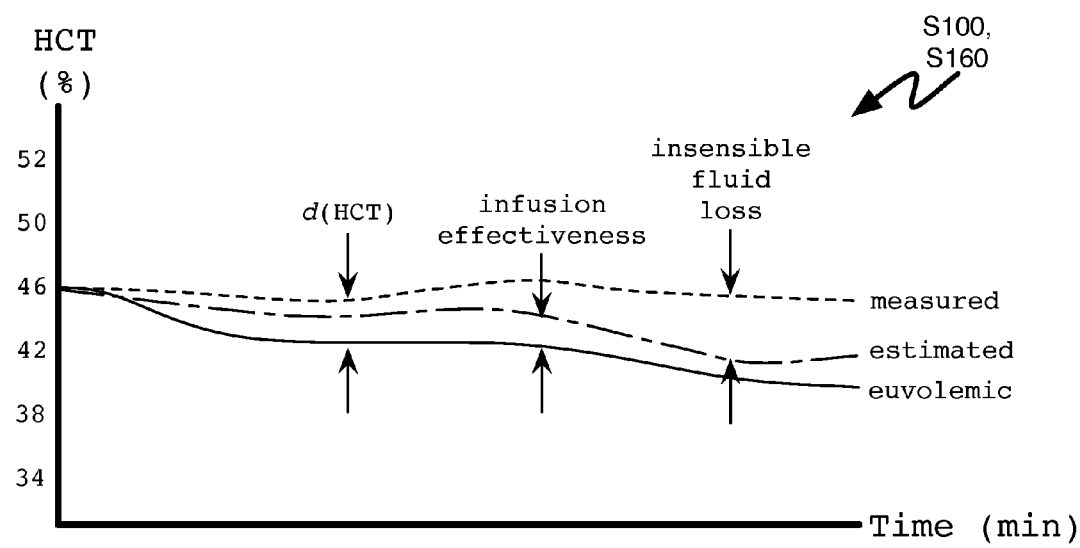

As shown in FIG. 7B, Block S160 can similarly monitor the patient's hematocrit and identify a patient need for a saline infusion or blood component (e.g., red blood cell) transfusion when the patient's (measured or estimated) hematocrit falls outside of a suitable range. The suitable hematocrit range can define a maximum patient hematocrit and a minimum patient hematocrit customized for the patient, such as based on the patient's age, gender, weight, and medical history and selected from a lookup table of hematocrit ranges. For example, as described in U.S. patent application Ser. No. 13/738,919 and U.S. patent application Ser. No. 13/894,054, Block S160 can receive an initial measured patient hematocrit and/or estimate an initial patient hematocrit (i.e., at the start of the surgery), such as based on patient age, gender, and medical history. Block S160 can then track changes in the patient's intracirculatory hematocrit over time (e.g., through a surgery) based on fluid infusions and transfusions, estimated blood loss (i.e., from processed images of bloodied substrates), estimated initial patient intracirculatory blood volume, patient weight, height, sex, age, and/or medical history (e.g., anemia), etc. Block S160 can further manipulate patient hematocrit, blood loss, infusion, transfusion, and/or other data to estimate a volemic status of the patient, the volemic status of the patient defining a difference between the current hematocrit of the patient and a target hematocrit of the patient, such as described in U.S. patent application Ser. No. 13/894,054.

By tracking total patient blood loss, total patient red blood cell loss, total patient hemoglobin loss, intracirculatory blood viscosity, and/or patient hematocrit over time and comparing any of these data to selected maximum and/or minimum values for the patient, Block S160 can predict a current or future patient transfusion (and infusion) need. For example, if a thirty-five year old female patient weighing 130 lbs can tolerate a loss of one liter of blood and a hematocrit between 0.36 and 0.44, Block S160 can determine that the patient requires a transfusion when estimated blood total loss surpasses one liter, such as plus or minus a factor of safety (e.g., 5%). Block S160 can similarly determine that the patient requires a transfusion when estimated intracirculatory hematocrit dips below 0.36, such as determined through methods described in U.S. patent application Ser. No. 13/894,054. Therefore, Block S160 can determine a current patient need for blood transfusion and cooperate with Block S170 to determine if autologous blood transfusion through blood cell salvage is suitable or practical to meet the patient's current blood transfusion need.

As described above, Block S160 can also extract trends in total patient blood loss, total patient hemoglobin loss, estimated patient intracirculatory hematocrit, etc. For example, Block S160 can identify a trending in a fill rate of the canister and/or a rate of gauze sponge user and corresponding blood content, and Block S160 can implement this data to estimate a future time at which the patient's intracirculatory blood volume, intracirculatory hematocrit, intracirculatory blood viscosity, and/or intracirculatory red blood cell content, etc. will fall outside of an acceptable range. In this example, Block S160 can determine that current total patient blood loss and patient intracirculatory hematocrit are within acceptable bounds but that an increasing blood loss rate will result in excessive blood loss at a particular time in the future (e.g., in approximately five minutes). Block S160 can thus cooperate with Block S170 to identify a feasibility of cell salvage to support autologous blood transfusion and thus meet the patient's fluid needs at a future time.

Figure 8:
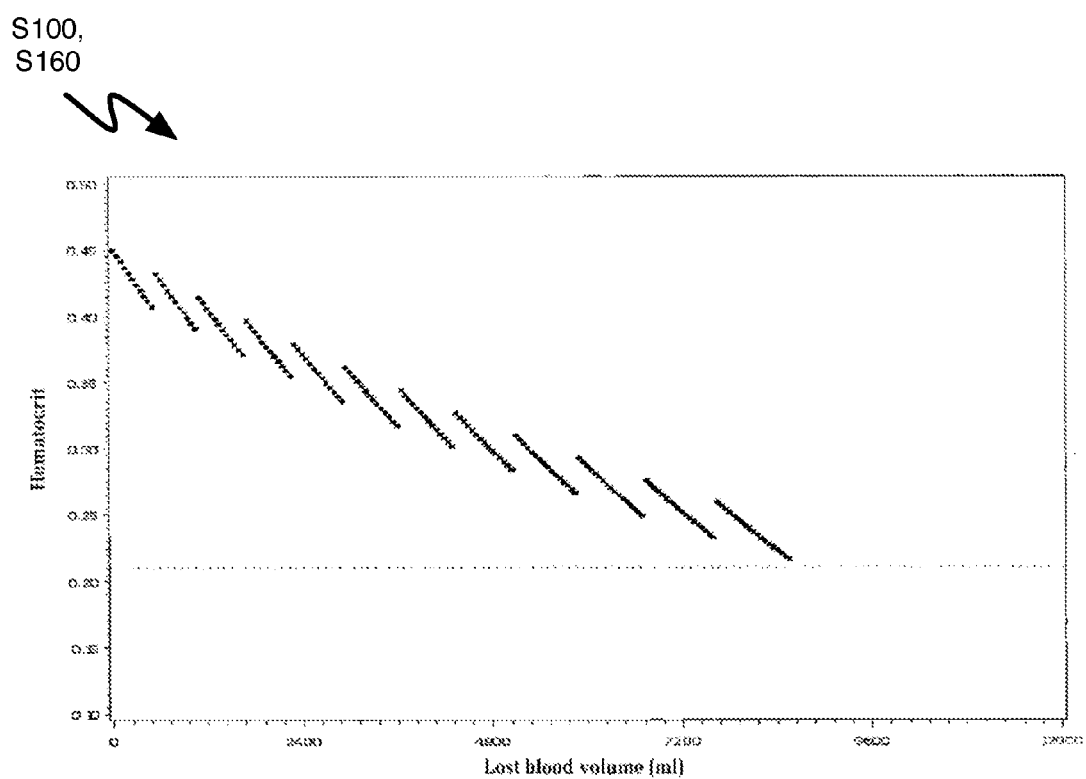
FIG. 8 is a graphical representation of one variation of the first method.

Generally, autologous blood transfusion can stay a patient need for allogeneic blood transfusion. As shown in FIG. 8, (from *A Mathematical Model of Cell Salvage Efficiency*, Waters, M D, Jonathan H., et al, which is incorporated in its entirety by this reference), autologous blood transfusion can enable continuous recycling of patient blood (or specifically the patient's red blood cells) to maintain patient circulatory (e.g., hemoglobin) needs without allogeneic blood transfusion. Based on projected patient blood loss, estimated blood recovery yields or efficiencies, etc., Block S160 can further estimate when allogeneic blood transfusion will be required to meet patient circulatory needs.

1.5 Blood Cell Salvage Cost

Figure 9:
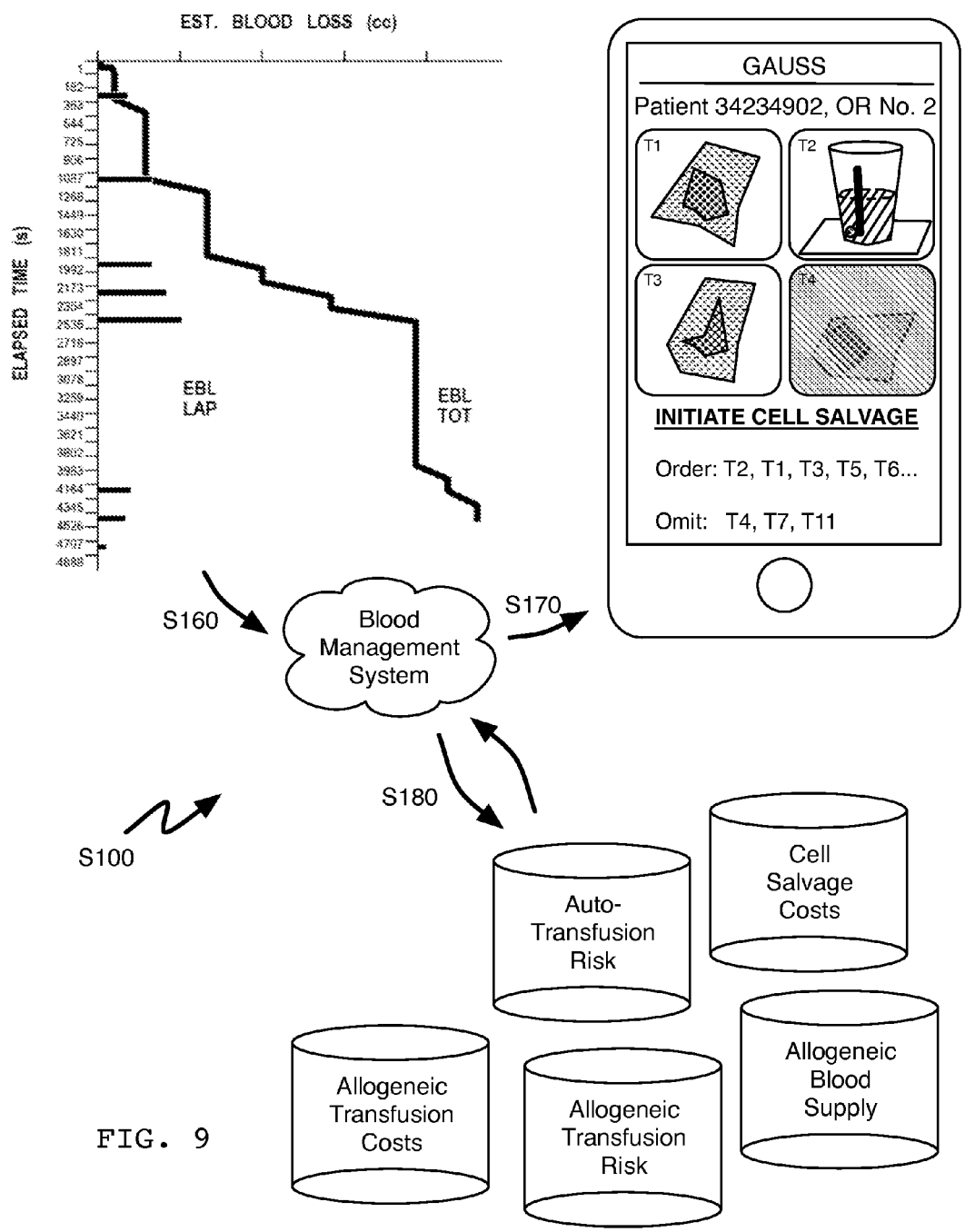
FIG. 9 is a flowchart representation of one variation of the first method.

As shown in FIG. 9, one variation of first method S100 includes Block S180, which recites estimating a blood component salvage cost. Generally, Block S180 functions to predict a cost associated with salvaging the estimated aggregate salvageable blood component (i.e., from Block S150) and compares this cost with the cost of allogeneic blood transfusion to estimate a financial feasibility of blood cell salvage to meet the patient's circulatory needs.

In one implementation, once patient blood transfusion needs are identified in Block S160, such as a minimum red blood cell volume for infusion to maintain the patient's hematocrit within an acceptable range, Block S180 accesses cost data pertaining to autologous and allogeneic blood transfusion. For example, a typical unit (i.e., liter) of allogeneic (i.e., donated) blood can be associated with a total fixed cost (e.g., ~1200 USD per liter in the United States for fiscal year 2012), including costs to procure the blood, to ship the blood to and from a blood bank, and to store the blood. Transfusion of a unit of allogeneic blood can also be associated with a fixed or variable cost, including anesthesiologist administration costs, insurance costs, and risk of patient complications from allogeneic transfusion. Block S180 can thus access these costs, such as from a remote database (e.g., via an Internet connection) or locally (e.g., from memory within a mobile computing device executing Blocks of first method S100. Block S180 can access these allogeneic-related costs as static costs that are generic to a time period (e.g., a month or a year) and a location, etc., or Block S180 can access these allogeneic-related costs as real-time, location-specific costs, such as based on real-time availability of blood of specific types within a local or internal blood bank and projected future blood supply and demand.

Block S180 can similarly access fixed and/or variable costs related to blood cell salvage. For example, blood cell salvage can be associated with time- and/or blood volume-dependent autotransfusion technician costs, blood salvage disposable costs (e.g., costs for wash kits, sponge soaking vessels, saline, cleaning agents, separated component holding bags, etc.), and risk of patient complications from autologous blood transfusion. Any of these costs can be fixed or variable, such as based on predefined costs or real-time, location-based supplies and demands for any of the foregoing blood cell salvage resources. Block S180 can also account for different bloodied substrates available for cell salvage and account for costs (e.g., cost of disposables) to remove blood from each. For example, Block S180 can account for a disposable tubing cost to pump fluid from the canister into a blood cell salvage machine and for a soaking basin and saline to soak blood out of gauze sponges.

Block S180 can therefore generate an estimated cost of allogeneic blood transfusion based on an estimated amount of available blood for cell salvage, types of substrates, autotransfusion technician costs, disposables cost. Block S180 can also account for a time to recover a volume of a blood component (e.g., red blood cells) via cell salvage and a risk to the patient in waiting to receive the volume of the blood component when estimating autologous blood transfusion cost. Block S180 can then compare the estimated autologous blood transfusion cost to a cost of allogeneic blood transfusion for a number of liters of blood meeting the patient's circulatory need, flag Block S170 to forego or postpone cell salvage if the estimated autologous blood transfusion cost exceeds the allogeneic blood transfusion cost, and pass autologous blood transfusion confirmation to Block S170 if the estimated autologous blood transfusion cost substantially equals or falls below the allogeneic blood transfusion cost.

Block S180 can also estimate patient risk associated with autologous and allogeneic blood transfusions. Generally, allogeneic blood transfusion can pose substantially greater risk to a patient than autologous blood transfusion, and Block S180 can account for these differences in risk to assess a "true" or projected cost of allogeneic and autologous blood transfusion. For example, allogeneic blood transfusion can expose the patient to the, bacteria, viruses, or other pathogens in the donated blood, excessive amounts of free hemoglobin, allergic reaction, transfusion-related acute lung injury (TRALI), febrile reaction, acute immune hemolytic reaction (i.e., the wrong blood type), delayed hemolytic reaction, etc., and Block S180 can access an associated cost for each of these risks, such as based on actuarial assessments and a cost per incident amortized over a patient population, and Block S180 includes these actuarial costs in a total estimate cost of allogeneic blood transfusion. Block S180 can apply similar risks and associated costs to autologous blood transfusion. However, Block S180 can function in any other way to estimate a blood component salvage cost and to compare this to an allogeneic blood transfusion cost.

1.6. Cell Salvage Prompts

As shown in FIGS. 2A and 2B, Block S170 of first method S100 recites, in response to the estimated aggregate salvageable blood component content exceeding a threshold salvageable blood component content, generating a prompt to salvage the blood component from fluid within the canister and from the gauze sponge. (Block S170 can similarly recite, in response to the estimated aggregate salvageable blood component content exceeding a threshold salvageable blood component content, generating a prompt to salvage the blood component from the first substrate and from the second substrate.) Generally, Block S170 functions to prompt or trigger cell salvage for autologous blood transfusion based on one or more of an estimated patient transfusion need (output in Block S160), an estimated aggregate salvageable blood component content from various substrates (output in Block S150), a blood cell salvage cost (output in Block S180), and an allogeneic blood transfusion cost (output in Block S180). Block S170 can therefore apply a cost comparison of allogeneic and autologous blood transfusion, an efficacy of autologous blood transfusion in meeting the patient's current or upcoming circulatory needs, and/or other related metrics output in various Blocks of first method S100 to automatically initiate blood cell salvage and/or to prompt a technician, nurse, or anesthesiologist, etc. to begin blood cell salvage. In particular, once Block S160 identifies a patient transfusion need, Block S150 verifies that autologous blood transfusion can fulfill the patient's need, and Block 180 determines that autologous blood transfusion is cost-effective, Block S170 can communicate an alarm to begin blood salvage to a suitable entity, such as a blood salvage technician, a nurse, or an anesthesiologist.

In one example, in a hospital with multiple operating rooms in use at any given time and with one blood salvage technician assigned to multiple active operating rooms at one time, Block S170 handles distribution of an alarm to the technician (e.g., via a SMS text message or native application notification on a smartphone) to notify the technician of a need to wash up, enter a particular operating room, and initiate blood salvage for autotransfusion for a specific patient. Block S170 can also trigger an audible alarm within the operating room or display a visual cue to begin blood cell salvage. For example, a tablet arranged in an operating room and implementing Blocks S110, S120, S130, and S140 can further implement Block S170 to display the prompt or notification to begin and/or prepare for blood cell salvage.

Alternatively, Block S170 can automatically initiate blood cell salvage. For example, a computer, computer network, server, tablet, smartphone, or other computing device implementing one or more Blocks of first method S100 can be electrically coupled or in wireless communication with a blood cell salvage machine within the operating room. In this example, the computing device can initiate transmission of fluid from the canister to the centrifuge vessel within the blood salvage machine (e.g., via a suction line by controlling valve and/or vacuum line), set a centrifuge speed and duration (as shown in FIG. 2), and automatically initiate separation of fluid, red blood cell, plasma, and waste components, etc. received from the canister.

However, Block S170 can function in any other way to trigger an alarm corresponding to, deliver a prompt or notification for, or automatically initiate blood component salvage from fluid within the canister and the sponge.

Figure 2:
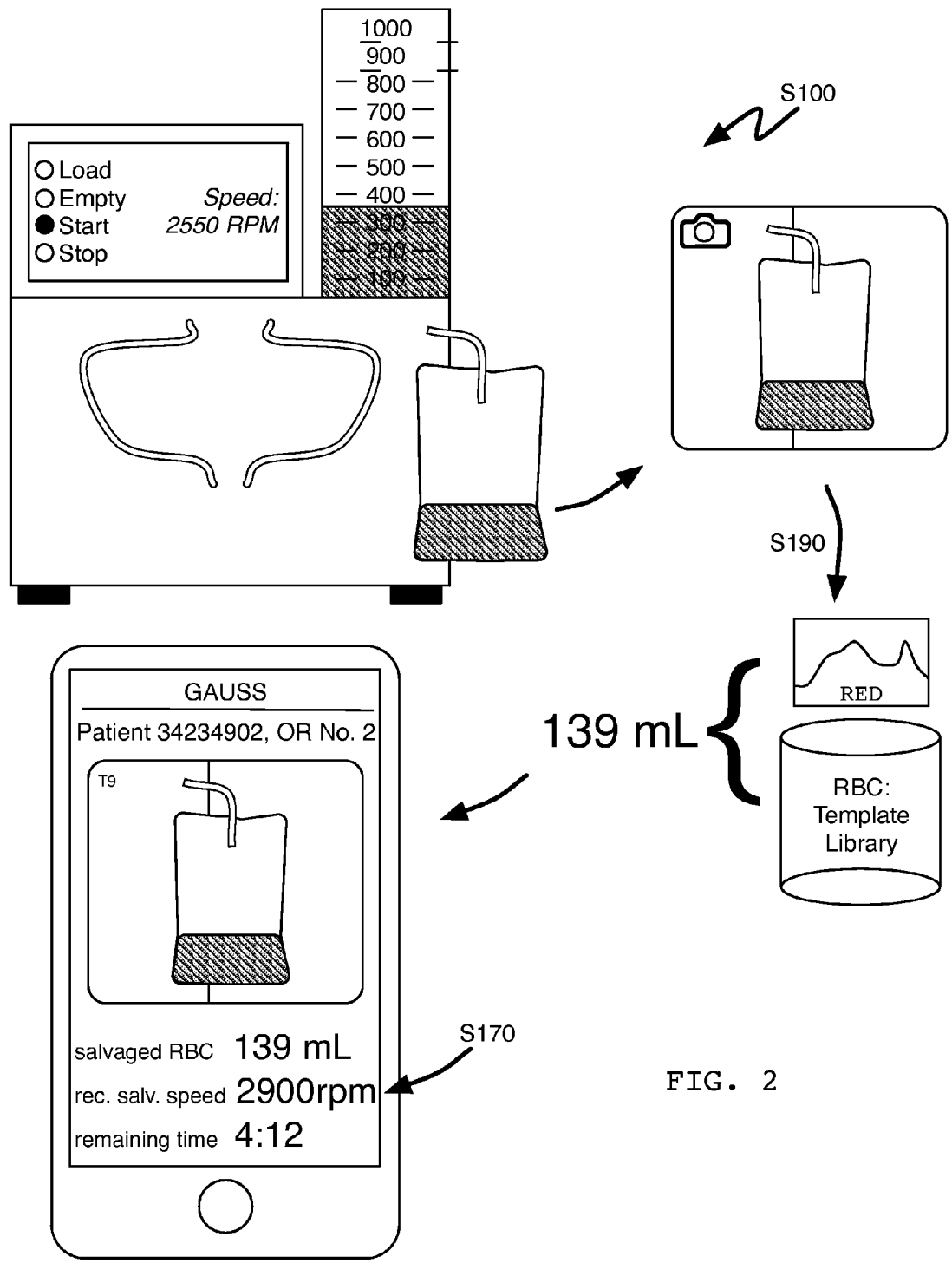
FIG. 2 is a flowchart representation of one variation of the first method.

As shown in FIGS. 1 and 2, Block S170 can further include recommending steps for recovery of fluid absorbed by the sponge. In this implementation, once Block S140 estimates a volume and quality of blood in a gauze sponge and determines that the gauze sponge is suitable for blood cell salvage, Block S170 can direct a user (e.g., an autotransfusion technician) in extracting fluid from bloodied sponges in preparation for blood cell salvage. In one example, Block S170 recommends a volume of soak fluid (e.g., saline) for a particular gauze sponge (or set of gauze sponges) based on the size of the gauze sponge and the estimated volume of blood in the sponge, such as to achieve efficient removal of the blood component from the gauze sponge with an effective starting concentration of the blood component in the soaking solution. In this implementation, Block S170 can thus guide the user in achieving a substantially repeatable starting concentration of blood, red blood cells, hemoglobin, etc. in soaking fluid used to extract blood from each sponge. For example, Block S170 can access optimum centrifuge speed, time, and/or other parameters for extraction of a particular blood component with a particular yield (i.e., loss percentage) based on a particular starting concentration of a blood component, and Block S170 can thus guide the user in achieving the particular starting concentration in the soaking solution by providing to the user a real-time directive to meet this concentration.

In another example, for a determined estimated blood volume or a particular sponge and an entered fluid soak volume (e.g., 200 mL of saline), Block S170 can recommend a particular centrifuge speed, time, and/or other parameter to achieve a certain yield (i.e., loss percentage) from a bloodied gauze sponge, such as based on an estimated initial concentration of soak fluid dispensed into the blood cell salvage machine. Furthermore, Block S170 can provide similar recommendations for soaking and/or recovering a blood component from multiple sponges simultaneously, such as in the same soak bath. Block S170 can also recommend a soak time, a soak fluid, or any other suitable action related to preparing a sponge for blood cell salvage.

In yet another example, Block S170 can prompt ordered or preferential cell salvage from various substrates, such as based on a cell salvage order for a set of gauze sponges specified in Block S140 based on blood component content in the gauze sponges in the set. Block S170 can thus guide progression of cell salvage from various substrates by prompting the user to select specific substrates (e.g., gauze sponges) for subsequent salvage. For example, Block S170 can display a sponge gauze number, barcode, QR code, or bucket (described above) on a mobile computing device (e.g., tablet) also executing other Blocks of first method S100 location within the operating room.

Block S170 can further include auto-filling a blood salvage form with patient- and salvage-related metrics. For example, Block S170 can collect estimate patient blood loss, estimated blood quality and quantity in various substrates, total recovered blood or blood component (e.g., red blood cells), etc. from various Blocks of first method S100, and Block S170 can automatically enter some or all of this data into a standardized digital form, such into a form similar to that shown in FIG. 6. Block S170 can subsequently transmit this digital form to a relevant entity, such as a hospital administrator or representative, an insurance company, a blood salvage technician, or a blood salvage operator or machine manufacturer.

As shown in FIG. 2, one variation of first method S100 includes Block S190, which recites identifying a blood transfusion bag in a third photographic image, the blood transfusion bag coupled to an output of the blood cell salvage machine, processing the third photographic image to estimate a volume of fluid in the translucent medical bag, extracting a color feature from a region of the third photographic image corresponding to the blood transfusion bag, estimating a blood component concentration within the blood transfusion bag based on the color feature, and estimating a blood component content within the blood transfusion bag based on the volume of fluid and the blood component concentration in the blood transfusion bag. Generally, Block S190 implement machine vision techniques to process an image of a transfusion bag coupled to a blood cell salvage machine to estimate an amount and/or quality of a blood component within the transfusion bag. In particular, Block S190 can implement methods and techniques described below in second method S200 to provide cell salvage feedback as and/or after the blood component is or has been salvaged from one or more substrates. For example, Block S190 can implement machine vision techniques described above, in second method S200 below, and in U.S. patent application Ser. Nos. 13/544,646 and 13/738,919 to estimate a volume or mass of red blood cells in a blood transfusion bag coupled to the cell salvage machine prior to transfusion into the patient.

One implementation of Block S190 includes, with an optical sensor, capturing an image of a bloodied fluid within a blood component separator of a blood salvage machine, extracting a color value from the image, and estimating a blood component salvage time from fluid within the blood salvage machine based on the extracted color value. Generally, in the implementation, Block S190 implements any of the foregoing machine vision techniques to associate a color value in an image with a blood-related metric. For example, Block 190 can capture and analyze an image of a bloodied fluid within a centrifuge of a blood salvage machine, extract a color from an area of the image corresponding to the fluid, implement a parametric or non-parametric model to analyze the area of the image, and determine a state of fluid and particulate (e.g., red blood cell) separation within the centrifuge. Block S190 can then correlate the state of separation with a remaining time to complete blood component salvage from the fluid, such as a time to achieve a target minimum blood component loss (e.g., <5% loss), as shown in FIG. 2. Based on the determination time to completion, Block S190 can further trigger an alarm to stop the blood salvage machine and initiate transfusion of the salvaged blood component back into the patient. Alternatively, Block S190 can interface with and/or control the cell salvage machine to automatically stop the blood salvage machine and/or begin autotransfusion. However, Block 190 can function in any other way to image and analyze fluid in the blood salvage machine.

However, first method S100 can function in any other way to estimate an amount of blood collected in various substrates, to estimate an amount of a blood component that can be salvaged from the collected blood, and to trigger or prompt blood cell salvage from the various substrates.

2. Second Method

Figure 10:
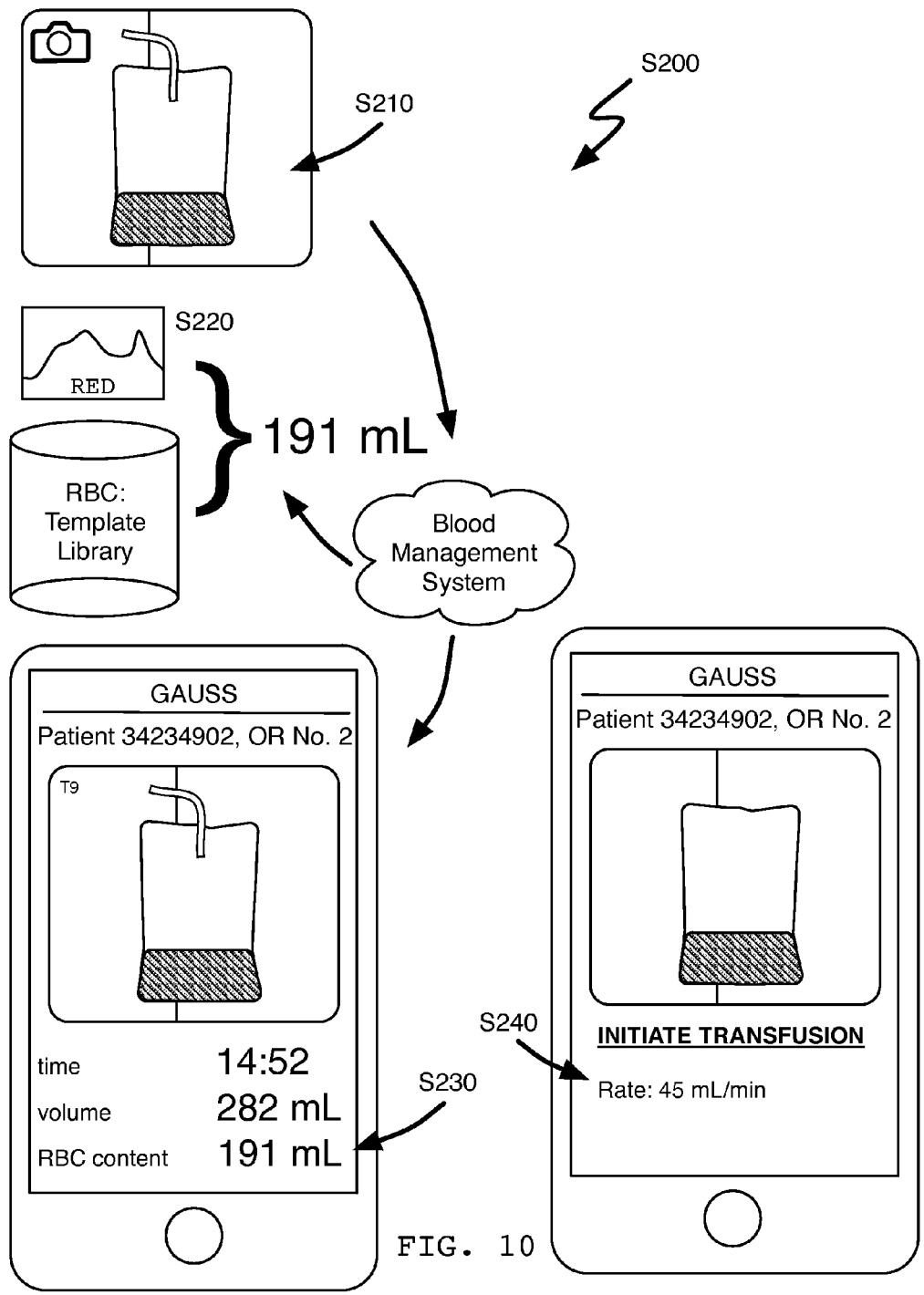
FIG. 10 is a flowchart representation of a second method of one embodiment of the invention.

As shown in FIG. 10, a second method S200 for setting a blood transfusion parameter for a patient includes: identifying a blood transfusion bag in a photographic image in Block S210; extracting a color feature from a region of the photographic image corresponding to the blood transfusion bag in Block S220; estimating a blood component content within the blood transfusion bag based on the color feature in Block S230; calculating a transfusion rate from the blood transfusion bag based on the blood component content within the blood transfusion bag and an estimated volemic status of the patient in Block S240.

Figure 11:
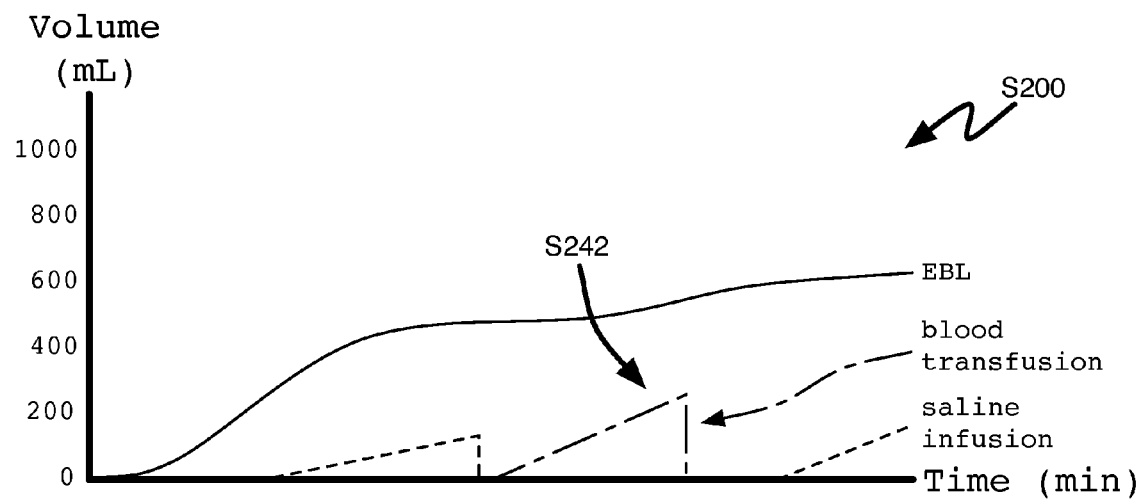
FIG. 11 is a graphical representation of one variation of the second method.

A variation of second method S200 recites: identifying a translucent medical bag in a photographic image and processing the photographic image to estimate a volume of fluid in the translucent medical bag in Block S210; extracting a color feature from a region of the photographic image corresponding to the translucent medical bag in Block S220; estimating a blood component concentration within the translucent medical bag based on the color feature and estimating a blood component content within the translucent medical bag based on the volume of fluid and the blood component concentration in the translucent medical bag in Block S230; and updating a blood loss history of the patient with the blood component content in Block S242 (shown in FIG. 11).

Generally, like Block S190 of first method S100 described above, second method S200 functions to process an image of an autologous transfusion bag and to estimate a content (e.g., volume, mass, etc.) of a blood component within the transfusion bag, such as during or after the transfusion bag is filled by a cell salvage machine and before the contents of the transfusion bag are transfused back into a patient. Second method S200 can similarly function to process an image of an autologous transfusion bag to quantify and/or qualify its contents prior to transfusion into a patient. Second method S200 can further process an image of other types of transparent medical bags (e.g., Foley bags) to determine content (e.g., presence of blood) and to update a patient blood loss or fluid history accordingly.

Like first method S100, Blocks of second method S200 can be implemented locally, such as on a tablet, smartphone, or other computing device within an operating room. Additionally or alternatively, Block of second method S200 can be implemented remotely, such as on a remote server or over a computer network. Furthermore, like first method S100, second method S200 can be implemented in an operating room during a surgery or in any other setting necessitating blood loss and/or blood transfusion management.

2.1 Image

One variation of second method S200 includes Block S202, which recites capturing the photographic image with a camera integrated into a mobile computing device. Generally, Block S202 can function like Block S10 or Block S130 of first method S100 to capture an image of a transparent bag, such as an allogeneic or autologous blood transfusion bag, an allogeneic or autologous blood component (e.g., plasma, red blood cell) bag, a salvaged blood component bag, or a urethral catheter (e.g., Foley) bag, a postpartum bag or drape, etc. Block S202 can capture images automatically, such as by implementing object recognition to detect a transparent bag in a field of view of a camera and the automatically triggering a shutter to capture an image, or Block S202 can collect images captured in response to manual input. Block S202 can also collect multiple images of a particular transparent bag over time, such as an image every ten seconds as a cell salvage machine fills an autologous transfusion bag or while a transfusion bag is emptied into a patient.

2.2 Identification

Block S210 of second method S200 recites identifying a blood transfusion bag in a photographic image. (Block S210 can similarly recite identifying a translucent medical bag in a photographic image.) Generally, Block S210 can implement machine vision to detect a transparent bag, such as an autologous or allogeneic blood transfusion bag or a Foley bag, in the photographic image. For example, Block S210 can implement functionality similar to that described in U.S. patent application Ser. Nos. 13/544,646 and 13/738,919 to identify the transparent bag in the image.

Block S210 can also identify the type of bag in the image, such as by implementing machine vision and/or object recognition to match regions of the image to template images of known bags or features of known bags. In one implementation, Block S210 identifies the type of bag (and an expected content of the bag) based on an identified shape of the bag in the image. For example, Block S210 can identify a bag with a rectangular perimeter as a blood transfusion bag and bag with a circular perimeter as a urethral catheter bag.

Alternatively, Block S210 can implement machine vision and/or optical character recognition to scan a barcode, printed or embossed text, or handwritten text on the bag. In this implementation, Block S210 can then apply text, figures, or code extracted from the image to identify the type and/or contents of the bag. In an example in which the bag is a blood transfusion bag, Block S210 can read a barcode on a sticker on the bag, access a database (e.g., a hospital or blood bank database) storing data linked to the barcode, and retrieve bag type- and/or content-related information from the database based on the barcode, such as an age, origin, type, and/or volume of blood in the bag. In this example, second method S200 can further log entry of the blood transfusion bag into the operating room, check the blood type within the bag against the patient's blood type, and update a blood inventory record for the corresponding operating room, transfusion center, blood collection center, health clinic, or hospital, etc. In this example, Block S210 can also retrieve a location from a computing device within the operating room, such as a Global Positioning System (GPS) location from a GPS sensor within a mobile computing device (e.g., smartphone or tablet) within the operating room, receive a target location for the transfusion bag from a blood tracking database, and then transmit delivery confirmation for the blood transfusion bag to the database once the GPS location from the mobile computing device falls with a threshold range of the target location associated with the blood transfusion bag.

Block S210 can also process the photographic image to estimate a volume of fluid in the translucent medical bag. For example, Block S210 can implement edge detection to identify the region of the photographic image corresponding to a blood transfusion bag and then estimate a volume of fluid in the blood transfusion bag based on a perimeter shape of the region. In another example, for a hanging transparent bag, Block S210 can identify in a region of the photographic image corresponding to the transparent bag, a volume marker printed on the transparent bag. In this example, Block S210 can then identify a fluid surface within the transparent bag and estimate a volume of fluid in the blood transfusion bag based on a proximity between the volume marker and the detected fluid surface. In yet another example, Block S210 can implement optical character recognition to identify text printed on an allogeneic blood transfusion bag and thus identify a volume of fluid in the blood transfusion bag based on the identified text.

However, Block S210 can function in any other way and implement any other method or technique to identifying and determine the volume of contents within a transparent bag shown in a photographic image.

2.3 Bag Content

Block S220 of second method S200 recites extracting a color feature from a region of the photographic image corresponding to the blood transfusion bag. Generally, Block S220 functions to extract one or more color-related features from the image, such as described above and in U.S. patent application Ser. Nos. 13/544,646 and 13/738,919.

In one implementation, Block S220 extracts a color value—in the red component space—from a region of the photographic image corresponding to the transparent bag and estimates a concentration of red blood cells in the blood transfusion bag based on the redness value. For example, Block S220 can correlate an opacity or "depth" of redness in the region of the image corresponding to the transparent bag with a concentration of red blood cells in the bag. In another example, Block S220 can extract, from a region of the photographic image, a second color value in the blue component space and/or a third color value in the green component space and estimate a concentration of free hemoglobin in the blood transfusion bag based on the color value, the second color value, and the third color value. In particular, in this example, Block S220 can differentiate between free hemoglobin and hemoglobin contained in red blood cells based on a combination of color values in multiple color spaces.

In yet another example, Block S220 can detect the presence of blood in the patient's urine based on a redness value exceeding a threshold redness value in a portion of an image corresponding to a catheter (e.g., Foley) bag. In a similar example in which Block S210 captures an image of a (autologous or allogeneic) plasma transfusion bag, Block S220 can extract a redness value from the image of the bag and correlate this redness with an amount of free hematocrit in the plasma bag, such as by implementing a parametric and/or non-parametric model. Because free hematocrit can inhibit oxygen release into tissue, second method S200 can implement the determined amount of free hematocrit in the transfusion bag to determine if the contents of the transfusion bag are suitable for transfusion into the patient, such as given patient plasma need based on a measured or predicted patient hematocrit and/or blood viscosity.

Block S230 of second method S200 recites estimating a blood component content within the blood transfusion bag based on the color feature. Generally, Block S230 can implement methods and techniques described in U.S. patent application Ser. Nos. 13/544,646 and 13/738,919 to implement a parametric and/or non-parametric model to estimate the red blood cell and hemoglobin content of the bag. In one implementation, Block S230 combines a transparent bag volume determined in Block S210 with a blood component concentration determined in Block S220 to estimate the mass, weight, volume, number, or other metric of the blood component (e.g., red blood cells, hemoglobin, etc.) in the transparent bag.

In one example, Block S230 estimates a red blood cell mass and 'purity' (i.e., content, percentage, etc. of other media) in an autologous blood transfusion bag. In this example, Block S230 can prompt a user (e.g., a nurse, autotransfusion technician, anesthesiologist, etc.) to being transfusion of the contents of the autologous blood transfusion bag into the patient, such as once a threshold autologous blood transfusion bag volume and/or red blood cell mass is collected in the autologous blood transfusion bag through cell salvage. In another example, Block S230 estimates a volume and quality (e.g., hematocrit and percentage of free hemoglobin) of fluid in an allogeneic blood transfusion bag and cooperates with Block S240 to determine a preferred flow rate for patient transfusion and/or with Block S242 to update a patient blood loss log with the foregoing blood transfusion data. In yet another example, Block S230 estimates a volume of red bloods cells and a corresponding volume of blood in a catheter bag and cooperates with Block S242 to update a patient blood loss log with the volume of blood lost by the patient into the catheter bag.

Block S242, which recites updating a blood loss history of the patient with the blood component content, can therefore receive a blood content estimation for a catheter or other fluid collection bag from Block S230 and insert this estimation into a blood loss record for the patient, as shown in FIG. 11. For example, Block S242 can insert a blood content estimate for a Foley bag into the patient's blood loss history to support substantially accurate estimation of total patient blood loss during a surgery. In another example, Block S242 can compare a blood content estimate for an autologous blood transfusion bag to a blood content estimate for substrates fed into a cell salvage machine to verify salvageable blood content estimates for the substrates. Block S242 can thus enable application of machine learning techniques to estimate blood component contents of various substrates in first method S100 by supplying data for actual salvaged blood component from various substrates. First method S100 can therefore apply estimated and measured savaged blood content comparisons output in Block S242 to improve one or more models described above and implemented in various Blocks of first method S100.

2.4 Flow Rate

Block S240 of second method S200 recites calculating a transfusion rate from the blood transfusion bag based on the blood component content within the blood transfusion bag and an estimated volemic status of the patient. Generally, Block S240 functions to calculate a preferred flow rate of blood (or blood component) from the transfusion bag into the patient based on the blood component content in the transparent (i.e., transfusion) bag and a predicted patient need for the blood component. For example, Block S240 can extrapolate a trend in patient blood loss from a series of bloodied substrates imaged and processed over time as described above to predict future, time-dependent changes in patient blood loss and then calculate a transfusion rate to achieve a target intracirculatory blood volume (i.e., quantity), hematocrit (i.e., quality), and/or viscosity (quality), etc. if the patient based on quality and quantity characteristics of blood in the transfusion bag and a predicted future quality and/or quantity status of the patient's circulatory system.

In one implementation, Block S240 implements methods and techniques described above and in U.S. patent application Ser. No. 13/894,054 to estimate a volemic status of the patient. For example, Block S240 can estimate an intracirculatory blood volume of the patient based on a patient blood loss history and an infusion history of the patient. In this example, Block S240 can subsequently calculate the transfusion rate of fluid from the blood transfusion bag to achieve a target hematocrit based on the intracirculatory blood volume of the patient. In another example, Block S240 can extrapolate a volemic status trend of the patient from a patient blood loss history and then calculate a preferred transfusion rate from the blood transfusion bag to offset a predicted future volemic status of the patient output from the volemic status trend of the patient.

Furthermore, Block S240 can track changes in patient blood loss (e.g., based on time-stamped images of bloodied substrates received and processed over time a described above), patient blood loss rates, quality and quantity of patient infusions over time, etc. and then implement this data to update (i.e., modify) the transfusion rate. In particular, Block S240 can monitor the volemic status of the patient over time (e.g., based on blood content estimations in subsequent bloodied substrates) and modify the transfusion rate (i.e., flow rate from a transfusion bag) to offset a current or predicted future change in the volemic status of the patient.

Figure 12:
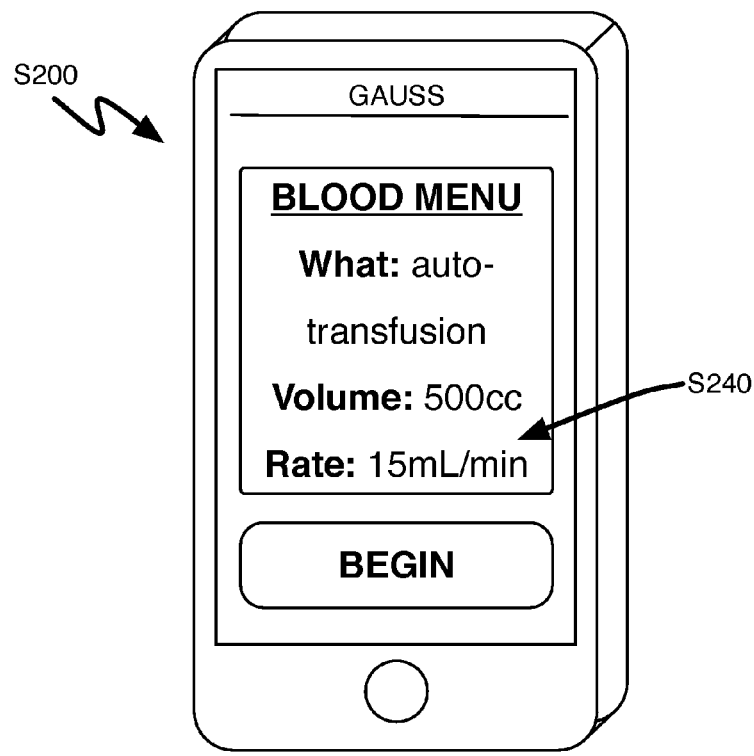
FIG. 12 is a graphical representation of one variation of the second method.

In one implementation, Block S240 displays the preferred transfusion rate (or a range of suitable transfusion rates) on a display integrated into a computing device arranged within the operating room and implementing one or more Blocks of first method S100 and/or second method S200, such as shown in FIGS. 10 and 12.

Block S240 can further integrate a constant or variable transfusion (i.e., flow) rate over time to estimate a total quantity of the component transfused into the patient. For example, Block S240 can define a target quantity of the blood component to transfuse into the patient based on a current and/or predicted future volemic status of the patient, and Block S240 calculate a transfusion stop time according to an instant at which the target quantity of the blood component is transfused from the transfusion bag into the patient. Block S240 can calculate the transfusion stop time in real-time and then trigger an alarm or transmit a notification to a user to prompt cessation of transfusion. Block S240 can additionally or alternatively estimate a transfusion stop asynchronously, such as before transfusion begins.

The foregoing Blocks of second method S200 can also capture and/or process subsequent images of the transparent (e.g., transfusion) bag, and Block S240 can manipulate volume and/or content estimations for the bag output in Block S230 for each subsequent image to estimate and track a flow rate from the bag into the patient. Block S240 can thus compare a measured flow rate to the target flow rate. Block S240 can implement this data to calibrate a flow meter coupled to the transfusion bag, to prompt a user to adjust a flow rate to within a suitable range of the target flow rate, and/or automatically adjust a flow rate from the bag, such as via an electromechanical flow meter coupled to a computing device executing Block S240.

However, Block S240 can function in any other way to calculate a transfusion rate from the blood transfusion bag, and second method S200 can implement this data to enable any other suitable functionality in any other suitable way.

The systems and methods of the preferred embodiment can be embodied and/or implemented at least in part as a machine configured to receive a computer-readable medium storing computer-readable instructions. The instructions are preferably executed by computer-executable components preferably integrated with the application, applet, host, server, network, website, communication service, communication interface, hardware/firmware/software elements of a user computer or mobile device, or any suitable combination thereof. Other systems and methods of the preferred embodiment can be embodied and/or implemented at least in part as a machine configured to receive a computer-readable medium storing computer-readable instructions. The instructions are preferably executed by computer-executable components preferably integrated by computer-executable components preferably integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but any suitable dedicated hardware device can (alternatively or additionally) execute the instructions.

As a person skilled in the art will recognize from the previous detailed description and from the figures and claims, modifications and changes can be made to the preferred embodiments of the invention without departing from the scope of this invention as defined in the following claims.

We claim:

1. A method for setting a blood transfusion parameter for a patient, the method comprising:
    identifying, at a computing system, a blood transfusion bag in a photographic image generated using an optical sensor in communication with the computing system, and, in a region of the photographic image, a fluid surface within the blood transfusion bag;
    extracting, at the computing system, a color feature from a region of the photographic image corresponding to the blood transfusion bag;
    identifying, at the computing system, a volume marker printed on the blood transfusion bag in the region of the photographic image;
    generating, at the computing system, an estimated volume of fluid in the blood transfusion bag based on the volume marker and the fluid surface;
    estimating, at the computing system, a blood component content within the blood transfusion bag based on the color feature and the estimated volume of fluid; and
    triggering transfusion from the blood transfusion bag based on the blood component content within the blood transfusion bag and an estimated volemic status of the patient.

2. The method of claim 1, wherein extracting the color feature from the region of the photographic image comprises extracting the color value in the red component space from the region of the photographic image, and wherein estimating the blood component content within the blood transfusion bag comprises estimating a concentration of red blood cells in the blood transfusion bag based on the redness value of the region of the photographic image.

3. The method of claim 2, wherein extracting the color feature from the region of the photographic image further comprises extracting a second color value in the blue component space and a third color value in the green component space from the region of the photographic image, and wherein estimating the blood component content within the blood transfusion bag further comprises estimating a concentration of free hemoglobin in the blood transfusion bag based on the color value, the second color value, and the third color value.

4. The method of claim 2, wherein identifying the blood transfusion bag in the photographic image comprises implementing optical character recognition to identify text printed on the blood transfusion bag and further comprising determining a volume of fluid in the blood transfusion bag based on identified text printed on the blood transfusion bag, estimating a red blood cell mass in the blood transfusion bag based on the concentration of red blood cells and the volume of fluid in the blood transfusion bag, and calculating a blood transfusion stop time based on the red blood cell mass in the blood transfusion bag and the volemic status of the patient.

5. The method of claim 1, further comprising
    receiving a second image of a physical substrate,
    extracting a feature from a region of the second image corresponding to the physical substrate,
    estimating the blood component content in the physical substrate based on the extracted feature,
    updating a blood loss history of the patient with the blood component content based on a timestamp of the second image,
    predicting a current hematocrit of the patient based on the blood loss history of the patient, and
    estimating the volemic status of the patient, the volemic status of the patient defining a difference between the current hematocrit of the patient and a target hematocrit of the patient.

6. The method of claim 5, wherein extracting the feature from the region of the second image comprises extracting the feature from the region of the second image corresponding to one of a suction canister, a gauze sponge, a surgical towel, and a surgical drape.

7. The method of claim 5, further comprising estimating an intracirculatory blood volume of the patient based on the blood loss history and an infusion history of the patient, wherein triggering transfusion from the blood transfusion bag comprises predicting achievement of the target hematocrit of the patient based on the intracirculatory blood volume of the patient, the current hematocrit of the patient, and the blood component content within the blood transfusion bag.

8. The method of claim 1, further comprising estimating a preferred transfusion rate from the blood transfusion bag to achieve a target hematocrit of the patient, based on the estimated volemic status and the blood component content within the blood transfusion bag.

9. The method of claim 5, further comprising extrapolating a volemic status trend of the patient from the blood loss history of the patient, wherein calculating the transfusion rate from the blood transfusion bag comprises calculating the transfusion rate from the blood transfusion bag to offset a predicted future volemic status of the patient based on the volemic status trend of the patient.

10. The method of claim 8, further comprising updating the transfusion rate over time based on the volemic status trend and an estimated blood component content in a second physical substrate.

11. The method of claim 1, wherein identifying the blood transfusion bag in the photographic image comprises identifying an autologous blood transfusion bag in the photographic image.

12. The method of claim 1, wherein identifying the blood transfusion bag in the photographic image comprises extracting a barcode from the region of the photographic image corresponding to the blood transfusion bag and retrieving, from a database, a set of data pertaining to allogeneic blood contained in the blood transfusion bag based on the extracted barcode.

13. The method of claim 12, further comprising capturing the photographic image with a camera integrated into a mobile computing device, receiving a Global Positioning System location from a corresponding sensor in the mobile computing device, and transmitting delivery confirmation for the blood transfusion bag to the database in response to the Global Positioning System location with a threshold range of a target location specified in the set of data pertaining to the blood transfusion bag.

14. The method of claim 13, wherein triggering transfusion from the blood transfusion bag comprises displaying an alarm to initiate transfusion from the blood transfusion bag on a display integrated into the mobile computing device.

15. The method of claim 1, wherein identifying the blood transfusion bag in the photographic image comprises implementing edge detection to identify the region of the photographic image corresponding to the blood transfusion bag and estimating a volume of fluid in the blood transfusion bag based on a perimeter shape of the region.

16. A method for setting a blood transfusion parameter for a patient, the method comprising:
    identifying, at a computing system, a blood transfusion bag in a photographic image generated using an optical sensor in communication with the computing system, comprising extracting a barcode, from a region of the photographic image corresponding to the blood transfusion bag and retrieving, from a database, a set of data pertaining to allogeneic blood contained in the blood transfusion bag based on the extracted barcode;
    extracting, at the computing system, a color feature from a region of the photographic image corresponding to the blood transfusion bag;
    identifying, at the computing system, a volume marker printed on the blood transfusion bag in the region of the photographic image;
    estimating, at the computing system, a blood component content within the blood transfusion bag based on the color feature; and
    triggering transfusion from the blood transfusion bag based on the blood component content within the blood transfusion bag and an estimated volemic status of the patient.

17. The method of claim 2, wherein extracting the color feature from the region of the photographic image comprises extracting the color value in the red component space from the region of the photographic image, and wherein estimating the blood component content within the blood transfusion bag comprises estimating a concentration of red blood cells in the blood transfusion bag based on the redness value of the region of the photographic image.

18. The method of claim 17, wherein extracting the color feature from the region of the photographic image further comprises extracting a second color value in the blue component space and a third color value in the green component space from the region of the photographic image, and wherein estimating the blood component content within the blood transfusion bag further comprises estimating a concentration of free hemoglobin in the blood transfusion bag based on the color value, the second color value, and the third color value.

19. The method of claim 17, wherein identifying the blood transfusion bag in the photographic image comprises implementing optical character recognition to identify text printed on the blood transfusion bag and further comprising determining a volume of fluid in the blood transfusion bag based on identified text printed on the blood transfusion bag, estimating a red blood cell mass in the blood transfusion bag based on the concentration of red blood cells and the volume of fluid in the blood transfusion bag, and calculating a blood transfusion stop time based on the red blood cell mass in the blood transfusion bag and the volemic status of the patient.

20. The method of claim 16, further comprising
    receiving a second image of a physical substrate,
    extracting a feature from a region of the second image corresponding to the physical substrate,
    estimating the blood component content in the physical substrate based on the extracted feature,
    updating a blood loss history of the patient with the blood component content based on a timestamp of the second image,
    predicting a current hematocrit of the patient based on the blood loss history of the patient, and
    estimating the volemic status of the patient, the volemic status of the patient defining a difference between the current hematocrit of the patient and a target hematocrit of the patient.

21. The method of claim 20, wherein extracting the feature from the region of the second image comprises extracting the feature from the region of the second image corresponding to one of a suction canister, a gauze sponge, a surgical towel, and a surgical drape.

22. The method of claim 20, further comprising estimating an intracirculatory blood volume of the patient based on the blood loss history and an infusion history of the patient, wherein triggering transfusion from the blood transfusion bag comprises predicting achievement of the target hematocrit of the patient based on the intracirculatory blood volume of the patient, the current hematocrit of the patient, and the blood component content within the blood transfusion bag.

23. The method of claim 16, further comprising estimating a preferred transfusion rate from the blood transfusion bag to achieve a target hematocrit of the patient, based on the estimated volemic status and the blood component content within the blood transfusion bag.

24. The method of claim 20, further comprising extrapolating a volemic status trend of the patient from the blood loss history of the patient, wherein calculating the transfusion rate from the blood transfusion bag comprises calculating the transfusion rate from the blood transfusion bag to offset a predicted future volemic status of the patient based on the volemic status trend of the patient.

25. The method of claim 23, further comprising updating the transfusion rate over time based on the volemic status trend and an estimated blood component content in a second physical substrate.

26. The method of claim 16, further comprising capturing the photographic image with a camera integrated into a mobile computing device, receiving a Global Positioning System location from a corresponding sensor in the mobile computing device, and transmitting delivery confirmation for the blood transfusion bag to the database in response to the Global Positioning System location with a threshold range of a target location specified in the set of data pertaining to the blood transfusion bag.

27. The method of claim 26, wherein triggering transfusion from the blood transfusion bag comprises displaying an alarm to initiate transfusion from the blood transfusion bag on a display integrated into the mobile computing device.

28. The method of claim 16, wherein identifying the blood transfusion bag in the photographic image comprises implementing edge detection to identify the region of the photographic image corresponding to the blood transfusion bag and estimating a volume of fluid in the blood transfusion bag based on a perimeter shape of the region.

* * * * *